United States Patent
Kahook et al.

(10) Patent No.: US 11,045,309 B2
(45) Date of Patent: Jun. 29, 2021

(54) INTRAOCULAR LENS DESIGNS FOR IMPROVED STABILITY

(71) Applicants: ClarVista Medical, Inc., Aliso Viejo, CA (US); The Regents of the University of Colorado, Denver, CO (US)

(72) Inventors: Malik Y. Kahook, Denver, CO (US); Glenn Sussman, Laguna Niguel, CA (US); Rudolph F. Zacher, Costa Mesa, CA (US); Paul J. McLean, North Oaks, MN (US); Robert E. Atkinson, Lake Elmo, MN (US)

(73) Assignees: The Regents of the University of Colorado, Denver, CO (US); Alcon Inc., Fribourg (CH)

( * ) Notice: Subject to any disclaimer, the term of this patent is extended or adjusted under 35 U.S.C. 154(b) by 0 days.

(21) Appl. No.: 15/585,901

(22) Filed: May 3, 2017

(65) Prior Publication Data
US 2017/0319332 A1   Nov. 9, 2017

Related U.S. Application Data

(60) Provisional application No. 62/332,163, filed on May 5, 2016.

(51) Int. Cl.
*A61F 2/16* (2006.01)

(52) U.S. Cl.
CPC .............. *A61F 2/1648* (2013.01); *A61F 2/16* (2013.01); *A61F 2002/169* (2015.04);
(Continued)

(58) Field of Classification Search
CPC .............. A61F 2/1648; A61F 2002/169; A61F 2002/16902
See application file for complete search history.

(56) References Cited

U.S. PATENT DOCUMENTS

| 3,937,222 A | 2/1976 | Banko |
| 4,092,743 A | 6/1978 | Kelman |

(Continued)

FOREIGN PATENT DOCUMENTS

| CA | 3 002 085 A1 | 5/2017 |
| EP | 0 478 929 A1 | 4/1992 |

(Continued)

OTHER PUBLICATIONS

PCT International Search Report and Written Opinion for International Application No. PCT/US2013/022752, dated Apr. 19, 2013 (12 pages).

(Continued)

*Primary Examiner* — Leslie Lopez
(74) *Attorney, Agent, or Firm* — Bookoff McAndrews, PLLC

(57) ABSTRACT

Intraocular lenses (IOLs) that improve lens stability by, for example, increasing anterior-posterior stiffness of the IOL, increasing anterior-posterior dimensions of the IOL and/or increasing contact area with the equator of the bag to resist movement of the IOL as the bag collapses over time. These IOLs may be non-modular (single component) or modular (multiple component). In modular embodiments, the IOL system may include intraocular base and optic components, which, when combined, form a modular IOL.

20 Claims, 13 Drawing Sheets

(52) U.S. Cl.
CPC ............... *A61F 2002/1681* (2013.01); *A61F 2002/1683* (2013.01); *A61F 2002/1689* (2013.01); *A61F 2220/0025* (2013.01); *A61F 2250/0036* (2013.01)

(56) References Cited

U.S. PATENT DOCUMENTS

| | | | |
|---|---|---|---|
| 4,168,547 A | 9/1979 | Konstantinov et al. | |
| 4,409,691 A | 10/1983 | Levy | |
| 4,435,856 A | 3/1984 | L'Esperance | |
| 4,681,102 A | 7/1987 | Bartell | |
| 4,693,245 A | 9/1987 | Pao | |
| 4,741,330 A | 5/1988 | Hayhurst | |
| 4,769,035 A | 11/1988 | Kelman | |
| 4,816,031 A | 3/1989 | Pfoff | |
| 4,828,558 A | 5/1989 | Kelman | |
| 4,842,601 A | 6/1989 | Smith | |
| 4,878,910 A | 11/1989 | Koziol et al. | |
| 4,911,715 A | 3/1990 | Kelman | |
| 4,932,971 A | 6/1990 | Kelman | |
| 4,950,472 A | 8/1990 | Smirmaul | |
| 4,960,418 A | 10/1990 | Tennant | |
| 5,026,396 A | 6/1991 | Darin | |
| 5,098,444 A | 3/1992 | Feaster | |
| 5,123,905 A | 6/1992 | Kelman | |
| 5,133,747 A | 7/1992 | Feaster | |
| 5,147,369 A | 9/1992 | Wagner | |
| 5,152,788 A | 10/1992 | Isaacson et al. | |
| 5,201,762 A | 4/1993 | Hauber | |
| 5,222,981 A | 6/1993 | Werblin | |
| 5,304,182 A | 4/1994 | Rheinsish et al. | |
| 5,354,335 A | 10/1994 | Lipshitz et al. | |
| 5,358,520 A | 10/1994 | Patel | |
| 5,366,502 A | 11/1994 | Patel | |
| 5,378,475 A | 1/1995 | Smith et al. | |
| 5,391,202 A | 2/1995 | Lipshitz et al. | |
| 5,395,378 A | 3/1995 | McDonald | |
| 5,410,375 A | 4/1995 | Fiala | |
| 5,417,369 A | 5/1995 | Lipson | |
| 5,507,805 A | 4/1996 | Koeniger | |
| 5,578,081 A | 11/1996 | McDonald | |
| 5,616,120 A | 4/1997 | Andrew et al. | |
| 5,628,795 A | 5/1997 | Langerman | |
| 5,628,798 A * | 5/1997 | Eggleston ............ | A61F 2/1694 623/6.11 |
| 5,728,155 A | 3/1998 | Anello et al. | |
| 5,769,890 A | 6/1998 | McDonald | |
| 5,814,103 A | 9/1998 | Lipshitz et al. | |
| 5,824,074 A | 10/1998 | Koch | |
| 5,860,985 A | 1/1999 | Anschutz | |
| 5,876,442 A | 3/1999 | Lipshitz et al. | |
| 5,895,422 A | 4/1999 | Hauber | |
| 5,902,598 A | 5/1999 | Chen et al. | |
| 5,928,283 A | 7/1999 | Gross et al. | |
| 5,944,725 A | 8/1999 | Cicenas et al. | |
| 5,964,802 A | 10/1999 | Anello et al. | |
| 5,968,094 A | 10/1999 | Werblin et al. | |
| 5,984,962 A | 11/1999 | Anello et al. | |
| 6,027,531 A | 2/2000 | Tassignon | |
| 6,066,171 A | 5/2000 | Lipshitz et al. | |
| 6,113,633 A | 9/2000 | Portney | |
| 6,136,026 A | 10/2000 | Israel | |
| 6,197,057 B1 | 3/2001 | Peyman et al. | |
| 6,197,058 B1 | 3/2001 | Portney | |
| 6,228,113 B1 | 5/2001 | Kaufman | |
| 6,231,603 B1 | 5/2001 | Lang et al. | |
| 6,277,146 B1 | 8/2001 | Peyman et al. | |
| 6,280,471 B1 | 8/2001 | Peyman et al. | |
| 6,358,280 B1 | 3/2002 | Herrick | |
| 6,413,276 B1 | 7/2002 | Werblin | |
| 6,423,094 B1 | 7/2002 | Sarfarazi | |
| 6,454,801 B1 | 9/2002 | Portney | |
| 6,464,725 B2 | 10/2002 | Skotton | |
| 6,488,708 B2 | 12/2002 | Sarfarazi | |
| 6,537,281 B1 | 3/2003 | Portney | |
| 6,551,354 B1 | 4/2003 | Ghazizadeh et al. | |
| 6,554,859 B1 | 4/2003 | Lang et al. | |
| 6,558,420 B2 | 5/2003 | Green | |
| 6,596,026 B1 | 7/2003 | Gross et al. | |
| 6,599,317 B1 | 7/2003 | Weinschenk, III et al. | |
| 6,616,692 B1 | 9/2003 | Glick et al. | |
| 6,638,304 B2 | 10/2003 | Azar | |
| 6,685,741 B2 | 2/2004 | Landreville et al. | |
| 6,695,881 B2 | 2/2004 | Peng et al. | |
| 6,764,511 B2 | 7/2004 | Zadno-Azizi et al. | |
| 6,767,363 B1 | 7/2004 | Bandhauer et al. | |
| 6,786,934 B2 | 9/2004 | Zadno-Azizi et al. | |
| 6,797,004 B1 | 9/2004 | Brady et al. | |
| 6,818,017 B1 | 11/2004 | Shu | |
| 6,846,326 B2 | 1/2005 | Zadno-Azizi et al. | |
| 6,858,040 B2 | 2/2005 | Nguyen et al. | |
| 6,899,732 B2 | 5/2005 | Zadno-Azizi et al. | |
| 6,926,736 B2 | 8/2005 | Peng et al. | |
| 6,960,231 B2 | 11/2005 | Tran | |
| 6,969,403 B2 | 11/2005 | Peng et al. | |
| 6,972,032 B2 | 12/2005 | Aharoni et al. | |
| 6,972,034 B2 | 12/2005 | Tran et al. | |
| 6,991,651 B2 | 1/2006 | Portney | |
| 7,008,447 B2 | 3/2006 | Koziol | |
| 7,041,134 B2 | 5/2006 | Nguyen et al. | |
| 7,081,134 B2 | 7/2006 | Cukrowski | |
| 7,087,080 B2 | 8/2006 | Zadno-Azizi et al. | |
| 7,097,660 B2 | 8/2006 | Portney | |
| 7,101,397 B2 | 9/2006 | Aharoni | |
| 7,118,596 B2 | 10/2006 | Zadno-Azizi et al. | |
| 7,122,053 B2 | 10/2006 | Esch | |
| 7,125,422 B2 | 10/2006 | Woods et al. | |
| 7,186,266 B2 | 3/2007 | Peyman | |
| 7,198,640 B2 | 4/2007 | Nguyen | |
| 7,220,278 B2 | 5/2007 | Peyman | |
| 7,223,288 B2 | 5/2007 | Zhang et al. | |
| 7,226,478 B2 | 6/2007 | Ting et al. | |
| 7,238,201 B2 | 7/2007 | Portney et al. | |
| 7,300,464 B2 | 11/2007 | Tran | |
| 7,316,713 B2 | 1/2008 | Zhang | |
| 7,452,378 B2 | 11/2008 | Zadno-Azizi et al. | |
| 7,582,113 B2 | 9/2009 | Terwee | |
| 7,591,849 B2 | 9/2009 | Richardson | |
| 7,645,299 B2 | 1/2010 | Koziol | |
| 7,662,179 B2 | 2/2010 | Sarfarazi | |
| 7,727,277 B2 | 6/2010 | Aharoni et al. | |
| 7,736,390 B2 | 6/2010 | Aharoni et al. | |
| 7,780,729 B2 | 8/2010 | Nguyen et al. | |
| 7,811,320 B2 | 10/2010 | Werblin | |
| 7,857,850 B2 | 12/2010 | Mentak et al. | |
| 7,871,437 B2 | 1/2011 | Hermans et al. | |
| 7,918,886 B2 | 4/2011 | Aharoni et al. | |
| 7,985,253 B2 | 7/2011 | Cumming | |
| 7,993,399 B2 | 8/2011 | Peyman | |
| 7,998,198 B2 | 8/2011 | Angelopoulos et al. | |
| 8,012,204 B2 | 9/2011 | Weinschenk, III et al. | |
| 8,034,106 B2 | 10/2011 | Mentak et al. | |
| 8,034,107 B2 | 10/2011 | Stenger | |
| 8,034,108 B2 | 10/2011 | Bumbalough | |
| 8,062,361 B2 | 11/2011 | Nguyen et al. | |
| 8,066,768 B2 | 11/2011 | Werblin | |
| 8,066,769 B2 | 11/2011 | Werblin | |
| 8,128,693 B2 | 3/2012 | Tran et al. | |
| 8,137,399 B2 | 3/2012 | Glazier et al. | |
| 8,167,941 B2 | 5/2012 | Boyd et al. | |
| 8,182,531 B2 | 5/2012 | Hermans et al. | |
| 8,187,325 B2 | 5/2012 | Zadno-Azizi et al. | |
| 8,197,541 B2 | 6/2012 | Schedler | |
| 8,273,123 B2 | 9/2012 | Ben Nun | |
| 8,287,593 B2 | 10/2012 | Portney | |
| 8,377,124 B2 | 2/2013 | Hong et al. | |
| 8,425,597 B2 | 4/2013 | Glick et al. | |
| 8,486,142 B2 | 7/2013 | Bumbalough | |
| 8,579,972 B2 | 11/2013 | Rombach | |
| 8,663,235 B2 | 3/2014 | Tassignon | |
| 8,728,158 B2 | 5/2014 | Whitsett | |
| 8,758,434 B2 | 6/2014 | Scott | |
| 8,900,300 B1 | 12/2014 | Wortz | |
| 9,011,532 B2 | 4/2015 | Bumbalough | |

(56) References Cited

U.S. PATENT DOCUMENTS

| | | |
|---|---|---|
| 9,095,424 B2 | 8/2015 | Kahook et al. |
| 9,125,736 B2 | 9/2015 | Kahook |
| 9,186,244 B2 | 11/2015 | Silvestrini et al. |
| 9,198,752 B2 | 12/2015 | Woods |
| 9,220,590 B2 | 12/2015 | Beer |
| 9,289,287 B2 | 3/2016 | Kahook |
| 9,364,316 B1 | 6/2016 | Kahook |
| 9,387,069 B2 | 7/2016 | Kahook et al. |
| 9,414,907 B2 | 8/2016 | Wortz et al. |
| 9,421,088 B1 | 8/2016 | Kahook et al. |
| 9,504,558 B2 | 11/2016 | Wortz et al. |
| 9,517,127 B2 | 12/2016 | Wortz et al. |
| 9,522,059 B2 | 12/2016 | Wortz et al. |
| 9,522,060 B2 | 12/2016 | Wortz et al. |
| 9,681,946 B2 | 6/2017 | Kahook et al. |
| 9,877,825 B2 | 1/2018 | Kahook et al. |
| 9,925,040 B2 | 3/2018 | Kahook et al. |
| 10,004,596 B2 | 6/2018 | Brady et al. |
| 10,028,824 B2 | 7/2018 | Kahook et al. |
| 10,080,648 B2 | 9/2018 | Kahook et al. |
| 10,111,745 B2 | 10/2018 | Silvestrini et al. |
| 10,159,564 B2 | 12/2018 | Brady et al. |
| 2002/0138140 A1 | 9/2002 | Hanna |
| 2003/0088253 A1 | 5/2003 | Seil |
| 2003/0144733 A1 | 7/2003 | Brady et al. |
| 2003/0158560 A1 | 8/2003 | Portney |
| 2004/0010310 A1 | 1/2004 | Peymen |
| 2004/0106993 A1 | 6/2004 | Portney |
| 2004/0148022 A1 | 7/2004 | Eggleston |
| 2004/0236422 A1 | 11/2004 | Zhang et al. |
| 2004/0243142 A1 | 12/2004 | Siepser |
| 2005/0015144 A1 | 1/2005 | Tran |
| 2005/0027354 A1 | 2/2005 | Brady et al. |
| 2005/0187621 A1 | 5/2005 | Brady |
| 2005/0125058 A1 | 6/2005 | Cumming et al. |
| 2005/0131535 A1 | 6/2005 | Woods |
| 2006/0111776 A1 | 5/2006 | Glick et al. |
| 2006/0253196 A1 | 11/2006 | Woods |
| 2006/0286147 A1 | 12/2006 | Salamone et al. |
| 2007/0123981 A1 | 5/2007 | Tassignon |
| 2008/0046077 A1 | 2/2008 | Cumming |
| 2008/0103592 A1 | 5/2008 | Maloney |
| 2008/0215147 A1 | 9/2008 | Werblin |
| 2009/0005864 A1 | 1/2009 | Eggleston |
| 2009/0062912 A1 | 3/2009 | Rombach |
| 2010/0016964 A1 | 1/2010 | Werblin |
| 2010/0204787 A1 | 8/2010 | Noy |
| 2010/0204790 A1 | 8/2010 | Whitsett |
| 2010/0298933 A1 | 11/2010 | Knox et al. |
| 2011/0040378 A1* | 2/2011 | Werblin ............... A61F 2/1648 623/6.34 |
| 2011/0054600 A1 | 3/2011 | Bumbalough |
| 2011/0251686 A1 | 10/2011 | Masket |
| 2011/0257742 A1 | 10/2011 | Bumbalough |
| 2011/0307058 A1 | 12/2011 | Beer |
| 2011/0313521 A1 | 12/2011 | Angelopoulos |
| 2012/0078364 A1 | 3/2012 | Stenger |
| 2012/0179249 A1 | 7/2012 | Coleman |
| 2012/0209305 A1 | 8/2012 | Deodhar et al. |
| 2013/0053954 A1 | 2/2013 | Rao et al. |
| 2013/0066422 A1 | 3/2013 | Dworschak et al. |
| 2013/0184815 A1 | 7/2013 | Roholt |
| 2013/0190868 A1 | 7/2013 | Kahook et al. |
| 2013/0296694 A1 | 11/2013 | Ehlers et al. |
| 2013/0304204 A1 | 11/2013 | Bumbalough |
| 2013/0310931 A1 | 11/2013 | Kahook et al. |
| 2014/0052246 A1 | 2/2014 | Kahook et al. |
| 2014/0081178 A1 | 3/2014 | Pletcher et al. |
| 2014/0084489 A1 | 3/2014 | Etzkorn |
| 2014/0085599 A1 | 3/2014 | Etzkorn |
| 2014/0085600 A1 | 3/2014 | Pletcher et al. |
| 2014/0085602 A1 | 3/2014 | Ho et al. |
| 2014/0087452 A1 | 3/2014 | Liu et al. |
| 2014/0088381 A1 | 3/2014 | Etzkorn et al. |
| 2014/0098226 A1 | 4/2014 | Pletcher et al. |
| 2014/0180403 A1 | 6/2014 | Silvestrini et al. |
| 2014/0180411 A1 | 6/2014 | Tornambe et al. |
| 2014/0192311 A1 | 7/2014 | Pletcher et al. |
| 2014/0194710 A1 | 7/2014 | Ho et al. |
| 2014/0194713 A1 | 7/2014 | Liu |
| 2014/0194773 A1 | 7/2014 | Pletcher et al. |
| 2014/0371852 A1* | 12/2014 | Aharoni ............... A61F 2/15 623/6.51 |
| 2015/0105760 A1 | 4/2015 | Rao et al. |
| 2015/0157452 A1 | 6/2015 | Maliarov |
| 2015/0230981 A1 | 8/2015 | Kahook et al. |
| 2016/0030161 A1 | 2/2016 | Brady et al. |
| 2016/0074154 A1 | 3/2016 | Woods |
| 2016/0128826 A1 | 5/2016 | Silvestrini et al. |
| 2016/0157995 A1 | 6/2016 | Beer |
| 2016/0184089 A1 | 6/2016 | Dudee et al. |
| 2016/0235524 A1 | 8/2016 | Wortz et al. |
| 2016/0235587 A1 | 8/2016 | Kahook et al. |
| 2016/0250020 A1 | 9/2016 | Kahook et al. |
| 2016/0310264 A1* | 10/2016 | Akura ............... A61F 2/1635 |
| 2016/0317286 A1 | 11/2016 | Brady et al. |
| 2016/0317287 A1 | 11/2016 | Silvestrini et al. |
| 2016/0331519 A1 | 11/2016 | Kahook et al. |
| 2016/0338825 A1 | 11/2016 | Wortz et al. |
| 2017/0119521 A1 | 5/2017 | Kahook et al. |
| 2018/0014928 A1 | 1/2018 | Kahook et al. |
| 2018/0161153 A1 | 6/2018 | Kahook et al. |
| 2018/0177639 A1 | 6/2018 | Rao et al. |
| 2018/0344453 A1 | 12/2018 | Brady et al. |
| 2018/0368974 A1 | 12/2018 | Kahook et al. |
| 2019/0000612 A1 | 1/2019 | Rao et al. |
| 2019/0021848 A1 | 1/2019 | Kahook et al. |
| 2019/0099263 A1 | 4/2019 | Brady et al. |

FOREIGN PATENT DOCUMENTS

| | | |
|---|---|---|
| EP | 1 138 282 A1 | 10/2001 |
| EP | 1 457 170 A1 | 9/2004 |
| EP | 1 743 601 A1 | 1/2007 |
| EP | 1 862 147 A1 | 12/2007 |
| EP | 2 042 124 A1 | 4/2009 |
| EP | 1 296 616 B1 | 5/2012 |
| EP | 1 871 299 B1 | 8/2012 |
| JP | 62-022641 | 1/1987 |
| JP | 04-505715 | 10/1992 |
| JP | 06-165793 | 6/1994 |
| JP | 63-089154 | 4/1998 |
| JP | 2003-505197 | 2/2003 |
| JP | 2003-524503 | 8/2003 |
| JP | 2007-512907 | 5/2007 |
| JP | 2008-525156 | 7/2008 |
| JP | 2008-532617 | 8/2008 |
| JP | 2010-516394 | 5/2010 |
| JP | 2012-040326 | 3/2012 |
| JP | 2013-512033 | 4/2013 |
| JP | 5705529 B2 | 4/2015 |
| RU | 2026652 C1 | 1/1995 |
| WO | WO 94/28825 A1 | 12/1994 |
| WO | WO 03/039335 A2 | 5/2003 |
| WO | WO 2006/118452 A1 | 11/2006 |
| WO | WO 2008/094518 A1 | 8/2008 |
| WO | WO 2010/002215 A2 | 1/2010 |
| WO | WO 2011/065833 A1 | 6/2011 |
| WO | WO 2012/023133 A1 | 2/2012 |
| WO | WO 2012/071146 A2 | 5/2012 |
| WO | WO 2013/112589 A1 | 8/2013 |
| WO | WO 2013/158942 A1 | 10/2013 |
| WO | WO 2014/197170 A1 | 12/2014 |
| WO | WO 2014/204575 A1 | 12/2014 |
| WO | WO 2016/022995 A2 | 2/2016 |
| WO | WO 2016/130209 A1 | 8/2016 |

OTHER PUBLICATIONS

PCT International Search Report and Written Opinion for International Application No. PCT/US2014/037646, dated Aug. 18, 2014 (14 pages).

(56) References Cited

OTHER PUBLICATIONS

PCT International Search Report and Written Opinion for International Application No. PCT/US2015/014046, dated Apr. 9, 2015 (14 pages).
PCT International Search Report and Written Opinion for International Application No. PCT/US2015/067035, dated Apr. 12, 2016 (17 pages).
PCT International Search Report and Written Opinion for International Application No. PCT/US2016/060350, dated Jan. 27, 2017 (14 pages).
PCT International Search Report and Written Opinion for International Application No. PCT/US2017/031066, dated Nov. 6, 2018 (9 pages).

* cited by examiner

INTRAOCULAR LENS DESIGNS FOR IMPROVED STABILITY

CROSS-REFERENCE TO RELATED APPLICATIONS

This application claims the benefits under 35 U.S.C. § 119(e) of priority to U.S. Provisional Patent Application No. 62/332,163, filed May 5, 2016, entitled "INTRAOCULAR LENS DESIGNS FOR IMPROVED STABILITY," which is incorporated herein by reference in its entirety.

This application is related to U.S. patent application Ser. No. 15/342,806, filed Nov. 3, 2016, entitled "MODULAR INTROCULAR LENS DESIGNS, TOOLS AND METHODS," U.S. patent application Ser. No. 15/218,658, filed Jul. 25, 2016, entitled "MODULAR INTRAOCULAR LENS DESIGNS, TOOLS AND METHODS," U.S. patent application Ser. No. 15/176,582, filed Jun. 8, 2016, entitled "MODULAR INTRAOCULAR LENS DESIGNS AND METHODS," U.S. patent application Ser. No. 15/150,360, filed May 9, 2016, entitled "MODULAR INTRAOCULAR LENS DESIGNS, TOOLS AND METHODS," now U.S. Pat. No. 9,421,088, U.S. Provisional Patent Application No. 62/332,163, filed May 5, 2016, entitled "INTRAOCULAR LENS DESIGNS FOR IMPROVED STABILITY," U.S. Provisional Patent Application No. 62/318,272, filed Apr. 5, 2016, entitled "MODULAR INTRAOCULAR LENS DESIGNS, TOOLS AND METHODS," U.S. patent application Ser. No. 15/054,915, filed Feb. 26, 2016, entitled "MODULAR INTRAOCULAR LENS DESIGNS AND METHODS," U.S. Provisional Patent Application No. 62/256,579, filed Nov. 17, 2015, entitled "MODULAR INTRAOCULAR LENS DESIGNS, TOOLS AND METHODS," U.S. Provisional Patent Application No. 62/250,780, filed Nov. 4, 2015, entitled "MODULAR INTRAOCULAR LENS DESIGNS, TOOLS AND METHODS," U.S. patent application Ser. No. 14/828,083, filed Aug. 17, 2015, entitled "MODULAR INTRAOCULAR LENS DESIGNS, TOOLS AND METHODS," now U.S. Pat. No. 9,364,316, U.S. patent application Ser. No. 14/808,022, filed Jul. 24, 2015, entitled "MODULAR INTRAOCULAR LENS DESIGNS AND METHODS," now U.S. Pat. No. 9,387,069, U.S. Provisional Patent Application No. 62/110,241, filed Jan. 30, 2015, entitled "MODULAR INTRAOCULAR LENS DESIGNS, TOOLS AND METHODS," U.S. patent application Ser. No. 14/610,360, filed Jan. 30, 2015, entitled "MODULAR INTRAOCULAR LENS DESIGNS, TOOLS AND METHODS," U.S. Provisional Patent Application No. 61/941,167, filed Feb. 18, 2014, entitled "MODULAR INTRAOCULAR LENS DESIGNS, TOOLS AND METHODS," U.S. patent application Ser. No. 13/969,115, filed Aug. 16, 2013, entitled "MODULAR INTRAOCULAR LENS DESIGNS & METHODS," now U.S. Pat. No. 9,289,287, U.S. patent application Ser. No. 13/937,761, filed Jul. 9, 2013, entitled "MODULAR INTRAOCULAR LENS DESIGNS AND METHODS," now U.S. Pat. No. 9,125,736, U.S. Provisional Patent Application No. 61/830,491, filed Jun. 3, 2013, entitled "MODULAR INTRAOCULAR LENS DESIGNS AND METHODS," U.S. patent application Ser. No. 13/748,207, filed Jan. 23, 2013, entitled "MODULAR INTRAOCULAR LENS DESIGNS & METHODS," now U.S. Pat. No. 9,095,424, U.S. Provisional Patent Application No. 61/589,981, filed on Jan. 24, 2012, entitled "LASER ETCHING OF IN SITU INTRAOCULAR LENS AND SUCCESSIVE SECONDARY LENS IMPLANTATION," and U.S. Provisional Patent Application No. 61/677,213, filed on Jul. 30, 2012, entitled "MODULAR INTRAOCULAR LENS DESIGNS & METHODS," each of which is incorporated herein by reference in its entirety.

TECHNICAL FIELD

The present disclosure generally relates to intraocular lenses (IOLs). More specifically, the present disclosure relates to embodiments of IOL designs for improved stability in the capsular bag.

BACKGROUND

The human eye functions to provide vision by transmitting light through a clear outer portion called the cornea, and focusing the image by way of a crystalline lens onto a retina. The quality of the focused image depends on many factors including the size and shape of the eye, and the transparency of the cornea and the lens.

When age or disease causes the lens to become less transparent (e.g., cloudy), vision deteriorates because of the diminished light, which can be transmitted to the retina. This deficiency in the lens of the eye is medically known as a cataract. An accepted treatment for this condition is surgical removal of the lens from the capsular bag and placement of an artificial intraocular lens (IOL) in the capsular bag. In the United States, the majority of cataractous lenses are removed by a surgical technique called phacoemulsification. During this procedure, an opening (capsulorhexis) is made in the anterior side of the capsular bag and a thin phacoemulsification-cutting tip is inserted into the diseased lens and vibrated ultrasonically. The vibrating cutting tip liquefies or emulsifies the lens so that the lens may be aspirated out of the capsular bag. The diseased lens, once removed, is replaced by an IOL.

After cataract surgery to implant an IOL, the optical result may be suboptimal. For example, shortly after the procedure, it may be determined that the refractive correction is erroneous leading to what is sometimes called "refractive surprise." This can be caused, in part, by post-operative movement of the IOL in the capsular bag. Effective lens position (ELP), often measured using Scheimpflug photography (e.g., Pentacam, Oculus, Germany), is a measure of the anterior-posterior distance from the anterior surface of the cornea to the anterior surface of the lens (a.k.a., anterior chamber depth or ACD). ELP can change significantly post-operatively, where a 1.0 mm shift in ELP corresponds to a 3.0 Diopter change in visual power. Thus, there is a need for an IOL that is more stable post-operatively to mitigate changes in ELP and reduce refractive surprise.

SUMMARY OF THE DISCLOSURE

Embodiments of the present disclosure provide IOLs that improve ELP stability by, for example, increasing anterior-posterior stiffness of the IOL, increasing anterior-posterior dimensions of the IOL and/or increasing contact area with the equator of the bag to resist movement of the IOL as the bag collapses over time. These IOLs may be non-modular, unitary, or monolithic (i.e., single component) or modular (multiple component). In modular embodiments, the IOL system may include intraocular base and optic components, which, when combined, form a modular IOL.

In one embodiment, a modular IOL includes an annular base having two radially outward extending haptics. The base may define a center hole and an inside perimeter, with a radially inward open recess around the inside perimeter.

The modular IOL system also includes a lens having an optical body with first and second tabs extending radially outward from the optical body. The base and lens may be assembled with the first and second tabs of the lens disposed in the recess of the base. The base may have an anterior-posterior dimension greater than the lens to increase the anterior-posterior stiffness of the assembly. The base may also have an anterior-posterior dimension approximating the anterior-posterior dimension inside the capsular bag (i.e., between leaflets of the capsular bag) for mitigating anterior-posterior shift in the bag.

In another embodiment, a modular IOL includes a base configured to receive a conventional lens. The base may be annular with a center hole, two radially outward extending haptics, and an inside ledge to receive a conventional lens with haptics. The base and lens may be assembled with the perimeter of the lens resting on the ledge of the base and the haptics of the lens extending through a slot in the base. Similar to other embodiments described herein, the base may have an anterior-posterior dimension greater than the lens to increase the anterior-posterior stiffness of the assembly. In addition, the base may also have an anterior-posterior dimension approximating the anterior-posterior dimension inside the capsular bag (i.e., between leaflets of the capsular bag) for mitigating anterior-posterior shift in the bag.

In yet another embodiment, a non-modular IOL includes an enlarged annular rim around an optic for increasing anterior-posterior rigidity. The enlarged annular rim may have an anterior-posterior dimension approximating the anterior-posterior dimension inside the capsular bag (i.e., between leaflets of the capsular bag). A gap in the rim maybe provided to enable folding for delivery via an injector. The rim may extend radially outward to form buttresses between the optic and haptics extending therefrom.

The IOLs according to embodiments of the present disclosure may be applied to a variety of IOL types, including fixed monofocal, multifocal, toric, accommodative, and combinations thereof. In addition, the IOLs according to embodiments of the present disclosure may be used to treat, for example: cataracts, large optical errors in myopic (near-sighted), hyperopic (far-sighted), and astigmatic eyes, ectopia lentis, aphakia, pseudophakia, and nuclear sclerosis.

Various other aspects and advantages of embodiments of the present disclosure are described in the following detailed description and drawings.

BRIEF DESCRIPTION OF THE DRAWINGS

The drawings illustrate example embodiments of the present disclosure. The drawings are not necessarily to scale, may include similar elements that are numbered the same, and may include dimensions (in millimeters) and angles (in degrees) by way of example, not necessarily limitation. In the drawings.

DETAILED DESCRIPTION

Reference will now be made in detail to examples of the present disclosure, which are illustrated in the accompanying drawings. Wherever possible, the same reference numbers will be used throughout the drawings to refer to the same or like parts. In the discussion that follows, relative terms such as "about," "substantially," "approximately," etc. are used to indicate a possible variation of ±10% in a stated value, numeric or otherwise, unless other variations are indicated.

Figure 1:
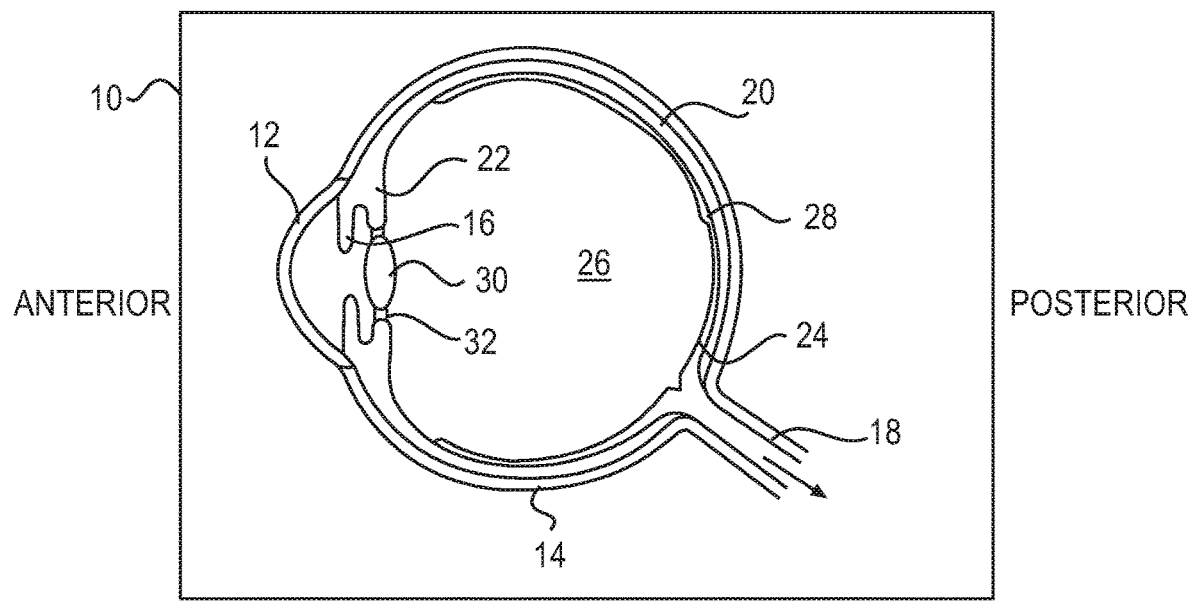
FIG. 1 is a schematic diagram of the human eye shown in cross-section.

With reference to FIG. 1, the human eye 10 is shown in cross section. The eye 10 has been described as an organ that reacts to light for several purposes. As a conscious sense organ, the eye allows vision. Rod and cone cells in the retina 24 allow conscious light perception and vision including color differentiation and the perception of depth. In addition, the human eye's non-image-forming photosensitive ganglion cells in the retina 24 receive light signals which affect adjustment of the size of the pupil, regulation and suppression of the hormone melatonin, and entrainment of the body clock.

The eye 10 is not properly a sphere; rather it is a fused two-piece unit. The smaller frontal unit, more curved, called the cornea 12 is linked to the larger unit called the sclera 14. The corneal segment 12 is typically about 8 mm (0.3 in) in radius. The sclera 14 constitutes the remaining five-sixths; its radius is typically about 12 mm. The cornea 12 and sclera 14 are connected by a ring called the limbus. The iris 16, the color of the eye, and its black center, the pupil, are seen instead of the cornea 12 due to the cornea's 12 transparency. To see inside the eye 10, an ophthalmoscope is needed, since light is not reflected out. The fundus (area opposite the pupil), which includes the macula 28, shows the characteristic pale optic disk (papilla), where vessels entering the eye pass across and optic nerve fibers 18 depart the globe.

Thus, the eye 10 is made up of three coats, enclosing three transparent structures. The outermost layer is composed of the cornea 12 and sclera 14. The middle layer consists of the choroid 20, ciliary body 22, and iris 16. The innermost layer is the retina 24, which gets its circulation from the vessels of the choroid 20 as well as the retinal vessels, which can be seen within an ophthalmoscope. Within these coats are the aqueous humor, the vitreous body 26, and the flexible lens 30. The aqueous humor is a clear fluid that is contained in two areas: the anterior chamber between the cornea 12 and the iris 16 and the exposed area of the lens 30; and the posterior chamber, between the iris 16 and the lens 30. The lens 30 is suspended to the ciliary body 22 by the suspensory ciliary ligament 32 (Zonule of Zinn), made up of fine transparent fibers. The vitreous body 26 is a clear jelly that is much larger than the aqueous humor.

The crystalline lens 30 is a transparent, biconvex structure in the eye that, along with the cornea 12, helps to refract light to be focused on the retina 24. The lens 30, by changing its shape, functions to change the focal distance of the eye so that it can focus on objects at various distances, thus allowing a sharp real image of the object of interest to be formed on the retina 24. This adjustment of the lens 30 is known as accommodation, and is similar to the focusing of a photographic camera via movement of its lenses.

The lens has three main parts: the lens capsule, the lens epithelium, and the lens fibers. The lens capsule forms the outermost layer of the lens and the lens fibers form the bulk of the interior of the lens. The cells of the lens epithelium, located between the lens capsule and the outermost layer of lens fibers, are found predominantly on the anterior side of the lens but extend posteriorly just beyond the equator.

The lens capsule is a smooth, transparent basement membrane that completely surrounds the lens. The capsule is elastic and is composed of collagen. It is synthesized by the lens epithelium and its main components are Type IV collagen and sulfated glycosaminoglycans (GAGs). The capsule is very elastic and so causes the lens to assume a more globular shape when not under the tension of the zonular fibers, which connect the lens capsule to the ciliary body 22. The capsule varies between approximately 2-28 micrometers in thickness, being thickest near the equator and thinnest near the posterior pole. The lens capsule may be involved with the higher anterior curvature than posterior of the lens.

Various diseases and disorders of the lens 30 may be treated with an IOL. By way of example, not necessarily limitation, an IOL according to embodiments of the present disclosure may be used to treat cataracts, large optical errors in myopic (near-sighted), hyperopic (far-sighted), and astigmatic eyes, ectopia lentis, aphakia, pseudophakia, and nuclear sclerosis. However, for purposes of description, the IOL embodiments of the present disclosure are described with reference to cataracts, which often occurs in the elderly population.

Figure 2:
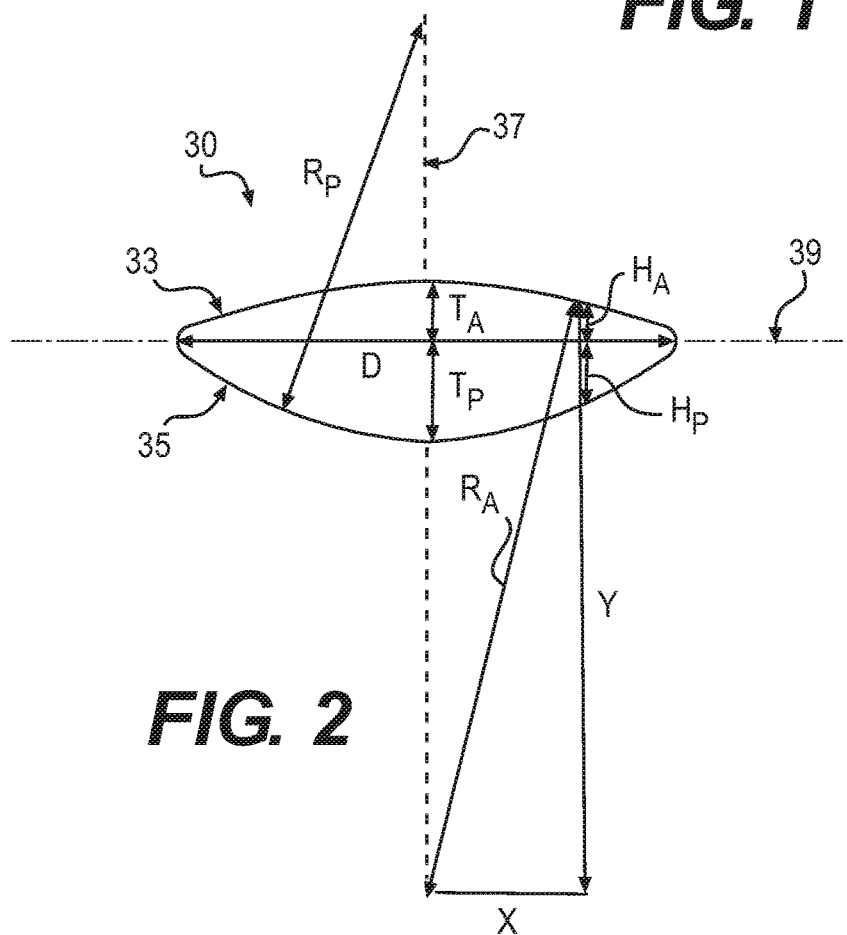
FIG. 2 is a schematic diagram of the lens of the human eye shown in sagittal cross-section.

As seen in FIG. 2, the shape of the lens 30 is generally symmetric about the visual axis 37. However, the lens 30 is not symmetric about the sagittal plane 39. Rather, the anterior side 33 of the lens 30 has a radius of curvature ($R_A$) that is greater than the radius of curvature ($R_P$) of the posterior side 35. The equatorial diameter (D) resides more anteriorly, with the posterior lens thickness ($T_P$) being greater than the anterior lens thickness ($T_A$).

Rosen et al. (2006) published data suggesting the equatorial diameter D, the posterior lens thickness $T_P$, the anterior lens thickness $T_A$, and the anterior radius of curvature $R_A$ change with age, whereas the posterior radius of curvature $R_P$ and the ratio $T_A/T_P$ remain constant. Using best-fit linear equations, Rosen et al. described the following age-dependent equations for these parameters (all in mm):

$D=0.0138(\pm0.002)*Age+8.7(\pm0.14)(R^2=0.57; p<0.0001)$;

$T_A=0.0049(\pm0.001)*Age+1.65(\pm0.075)(R^2=0.45; p<0.0001)$;

$T_P=0.0074(\pm0.002)*Age+2.33(\pm0.11)(R^2=0.44; p<0.0001)$;

$R_A=0.046(\pm0.017)*Age+7.5(\pm1.13)(R^2=0.27; p=0.016)$;

$R_P=-5.5(\pm0.9)$; and $T_A/T_P=0.70(\pm0.13)$.

These data or other empirically measured data may be used to describe the shape and size of the lens for a particular age group, such as cataracts in elderly patients at a mean age of 70, by way of example, not limitation. Such data may be useful to determine the space available for an intraocular implant to be placed in the capsular bag. For example, assume an ocular implant (such as an IOL) is to be centered in the equatorial plane, with an anterior-posterior height "H" at radial distance "X" from its center point. Also assume it is desired to have the anterior and posterior sides of the implant at radial distance X come into contact with the walls of the capsular bag to mitigate migration of the implant. Mathematical modeling may be used to determine the height (H) of the lens capsule at any given radial distance (X) from the visual axis 37 along the equatorial plane.

The total height H is equal to the sum of the anterior height ($H_A$) and the posterior height ($H_P$). The anterior height ($H_A$) may be given by the equation $H_A=Y-(R_A-T_A)$. While $R_A$ and $T_A$ are empirically known, the distance (Y) from the equatorial plane may be given by the equation $Y=(R_A^2-X^2)^{\wedge}0.5$. Combining these equations, the anterior height may be given by $H_A=(R_A^2-X^2)^{\wedge}0.5-(R_A-T_A)$, and solved using empirical data. The posterior height ($H_P$) may be similarly calculated using the posterior radius ($R_P$) and posterior thickness ($T_P$) solved using empirical data. Adding the posterior height ($H_P$) to the anterior height ($H_A$) provides the total height (H) at a distance (X) from the visual axis. Thus, the desired height (H) of the intraocular implant at radial distance X may be estimated such that the implant is in contact with the anterior and posterior walls of the capsular bag. Alternative mathematical models as described in the literature may be used as well.

The following detailed description describes various embodiments of modular and non-modular IOL systems. Features described with reference to any one embodiment may be applied to and incorporated into other embodiments.

Figure 3A:
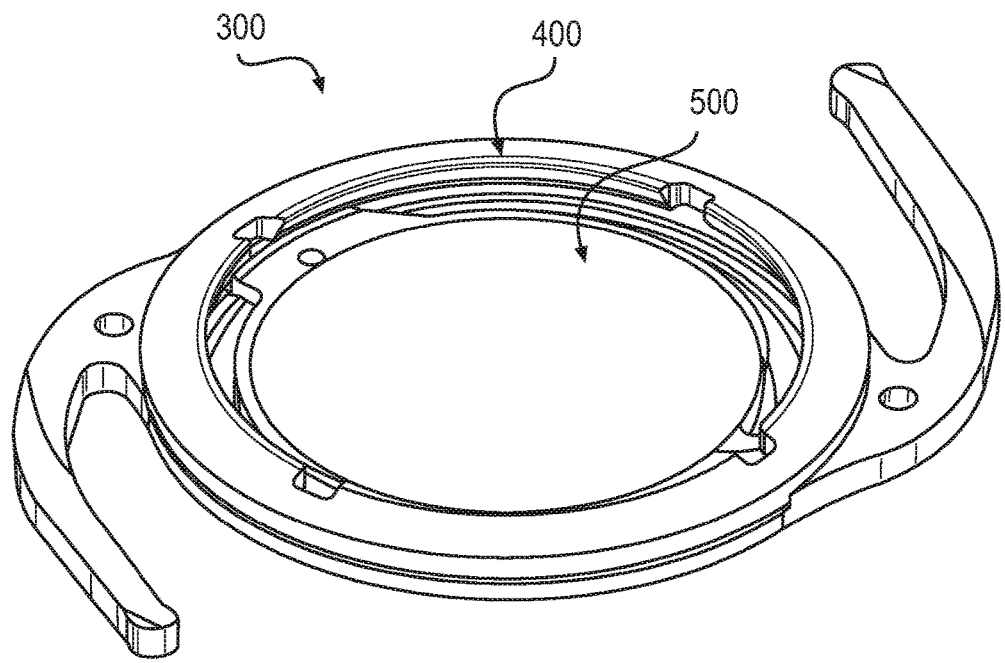
FIG. 3A is a perspective view of a modular IOL according to the present disclosure.

With reference to FIG. 3A, a base 400 and a lens 500 form an embodiment of a modular IOL 300 when assembled. A general description of the modular IOL 300 follows, with further detailed provided in U.S. Provisional Patent Application No. 62/318,272, which is hereby fully incorporated by reference.

Figure 4A:
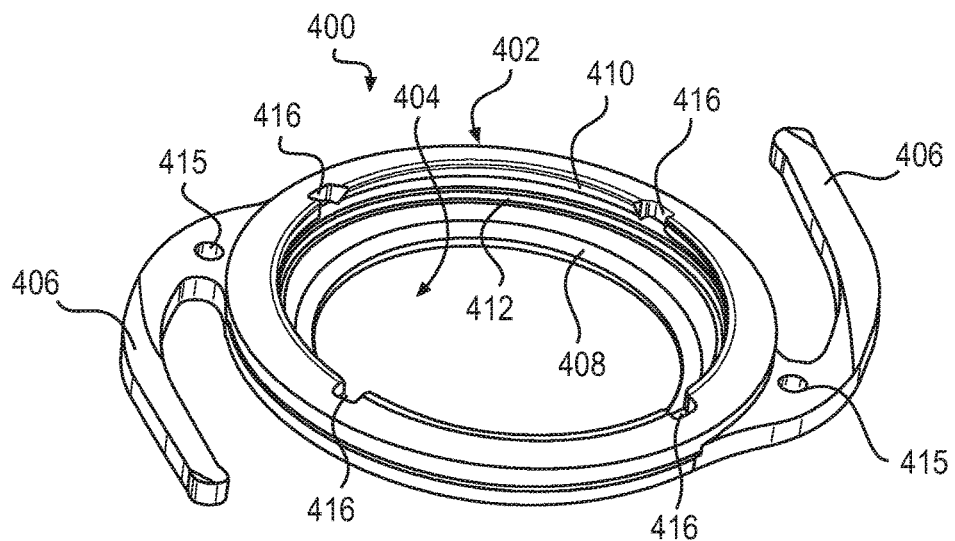
FIGS. 4A-4D are perspective, top, cross-sectional and detailed views, respectively, of the base of the modular IOL shown in FIG. 3A.
Figure 4B:
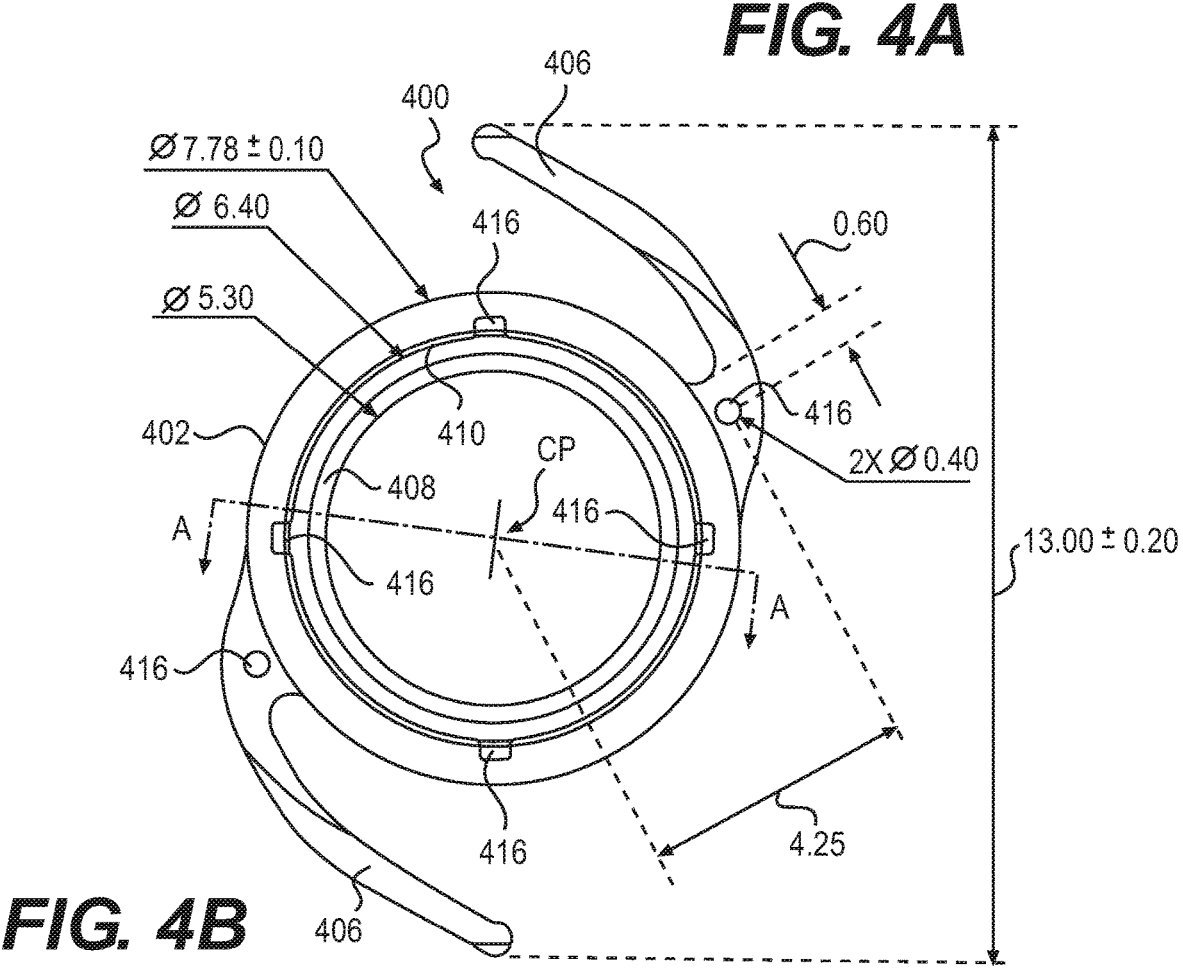
Figure 4C:
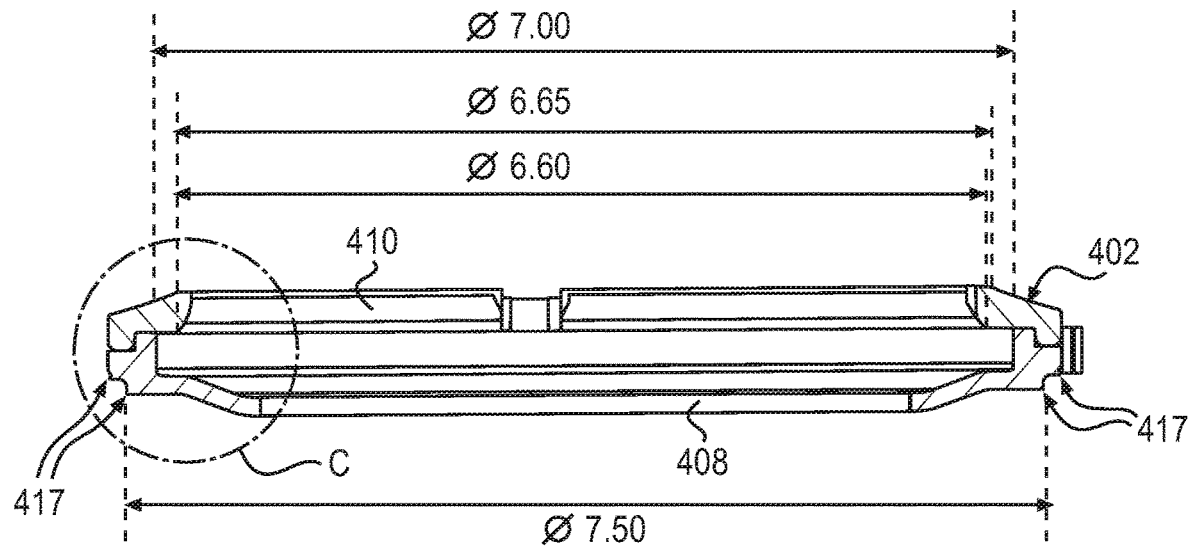
Figure 4D:
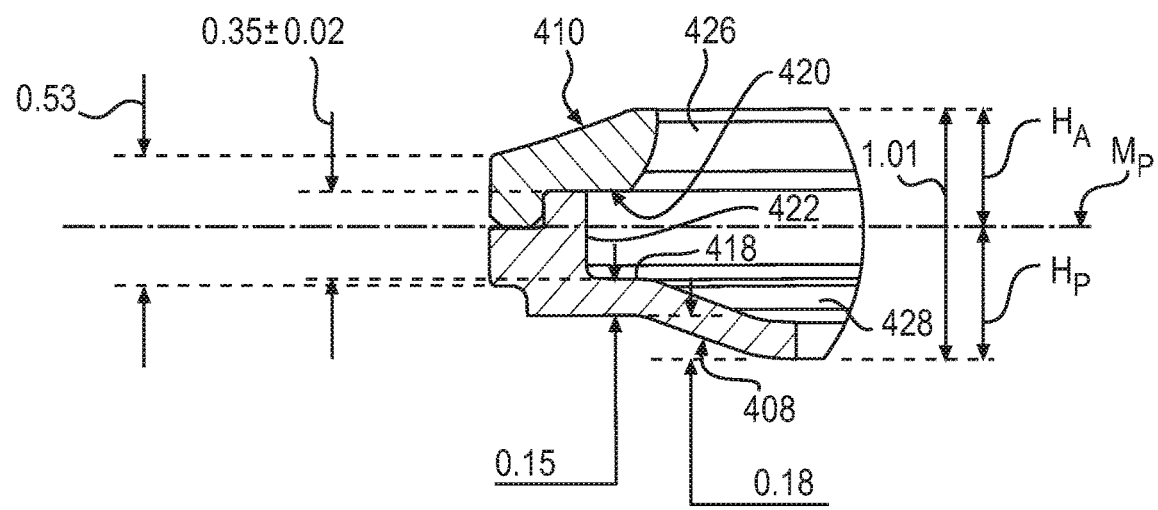

With reference to FIGS. 4A-4D, the base 400 is shown in more detail. FIG. 4A is a perspective view, FIG. 4B is a top view, FIG. 4C is sectional view taken along line A-A in FIG. 4B, and FIG. 4D is a detailed sectional view of circle C in FIG. 4C. Dimensions (mm) are given by way of example, not necessarily limitation.

The base 400 includes an annular ring 402 defining a center hole 404. A pair of haptics 406 extend radially outward from the annular ring 402. The annular ring 402 includes a lower rim 408, an upper rim 410 and an inward-facing recess 412, into which the lens 500 may be inserted to form modular IOL 300.

The upper rim 410 of annular ring 402 may include one or more notches 416 to provide access for a probe (e.g., Sinskey hook) intra-operatively, which allows the base 400 to be more easily manipulated. The haptics 406 may include holes 415 adjacent the annular ring 402 for the same purpose as notches 416. A pair of square edges 417 may extend around the posterior periphery of the annular ring 402 to help reduce cellular proliferation (posterior capsular opacification or PCO) onto the lens 500.

With specific reference to FIG. 4D, the deep portion of the recess 412 may have a squared profile defined by horizontal posterior surface 418, a horizontal anterior surface 420 and a vertical lateral or outer surface 422. The recess may also include a flared anterior surface 426 extending radially inward and anteriorly outward from the horizontal anterior surface 420, and a flared posterior surface 428 extending radially inward and posteriorly outward from the horizontal posterior surface 418. The inside diameter of the posterior rim 408 may be smaller than the inside diameter of the anterior rim 410. With this arrangement, the lens 500 may be placed through the circular opening defined by the anterior rim 410 to land or rest upon the posterior rim, and the flared anterior wall 426 together with the flared posterior wall 428 may act as a funnel to guide the tabs 504 and 506 of the lens 500 into the deep portion of the recess 412. When fully seated in the recess 412, the horizontal posterior wall 418, the horizontal anterior wall 420 and the vertical lateral wall 422 form a keyed geometry with the corresponding horizontal and vertical sides of the tabs 504 and 506 to limit movement of the lens 500 relative to the base 400 in anterior, posterior and radial directions.

As best seen in FIG. 4D, the base 400 may have an anterior-posterior height of $H=H_A+H_P$, where H is approximately 1 mm, $H_A$ is approximately 0.5 mm at a radial distance of approximately 3.2 mm from the center point CP, and $H_P$ is approximately 0.5 mm at a radial distance of 2.65 mm from the center point CP. However, as described previously, the posterior thickness $T_P$ of the native lens 30 is greater than the anterior thickness $T_A$ of the native lens 30. Therefore, these relative dimensions may be adjusted. For example, $H_P$ may be made greater than $H_A$ such that the sagittal mid-plane MP of the base 400 is aligned (+/−0.5 mm) with the equatorial plane of the lens 30 when the modular IOL 300 is implanted in the capsular bag. The ratio $H_A/H_P$ may be constant at approximately 0.7 (±0.3), for example. In addition, H may be selected such that the anterior-most portion of the anterior rim 410 is in close proximity (within 0.5 mm) to the anterior side 33 of the lens 30 and the posterior-most portion of the posterior rim 408 is in close proximity (within 0.5 mm) to the posterior side 35 of the lens 30 when implanted in the capsular bag. Thus, by way of example, not limitation, $H_A$ may be approximately 0.5 mm to 1.0 mm at a radial distance of approximately 2.75 mm to 3.25 mm from the center point CP, and $H_P$ may be approximately 0.75 mm to 1.5 mm at a radial distance of 2.25 mm to 2.50 mm from the center point CP, maintaining a constant ratio $H_A/H_P$ of approximately 0.7 (±0.3), for example.

Figure 5A:
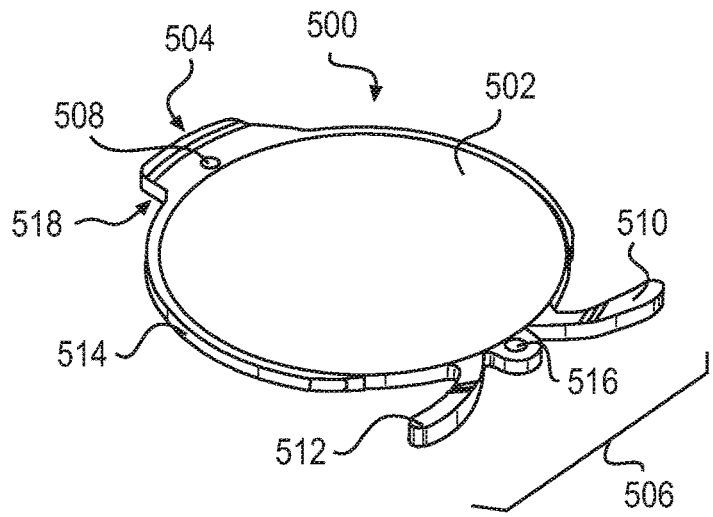
FIGS. 5A-5E are perspective, top, cross-sectional and detailed views, respectively, of the lens of the modular IOL shown in FIG. 3A.
Figure 5B:
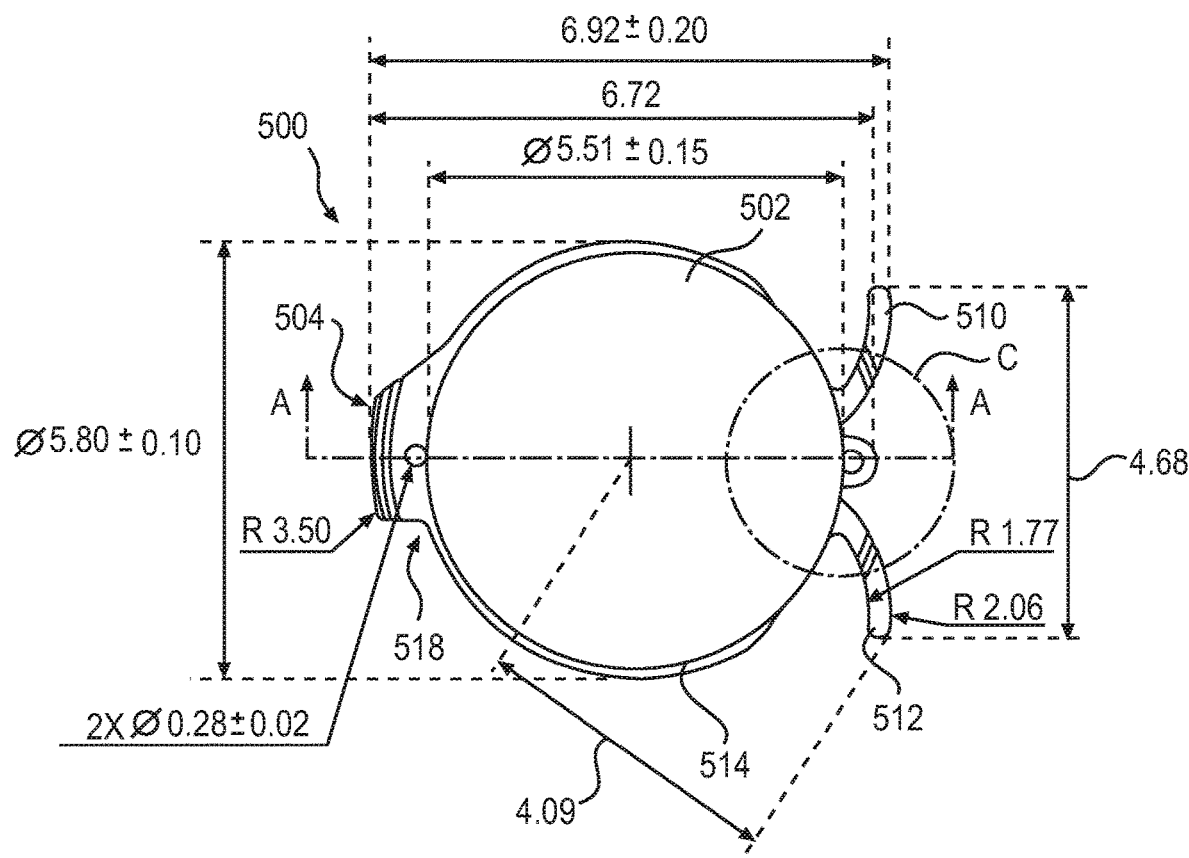
Figure 5C:
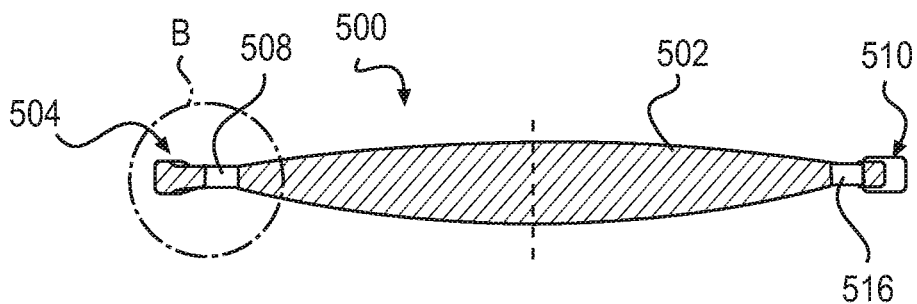
Figure 5D:
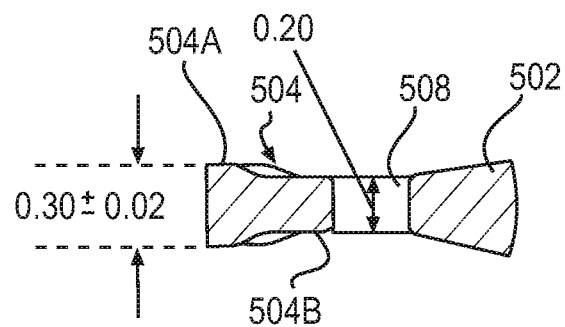
Figure 5E:
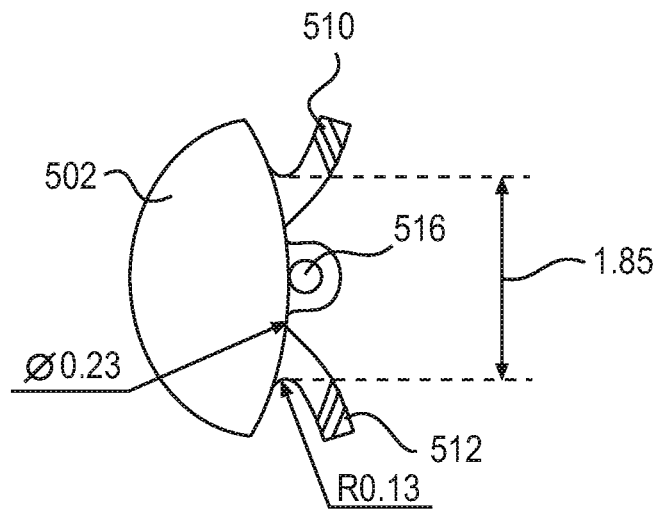

With reference to FIGS. 5A-5E, the lens 500 is shown in more detail. FIG. 5A is a perspective view, FIG. 5B is a top view, FIG. 5C is sectional view taken along line A-A in FIG. 5B, FIG. 5D is a detailed sectional view of circle B in FIG. 5C, and FIG. 5E is a detailed top view of circle C in FIG. 5B. Dimensions (mm) are given by way of example, not necessarily limitation.

The lens 500 may include an optic portion 502 and one or more tabs 504 and 506. As shown, tab 504 is fixed, whereas tab 506 may be actuated. Fixed tab 504 may include a thru hole 208 so that a probe (e.g., Sinskey hook) or similar device may be used to engage the hole 208 and manipulate the tab 504. Actuatable tab 506 may be actuated between a compressed position for delivery into the hole 404 of the base 400, and an uncompressed extended position (shown) for deployment into the recess 412 of the base 400, thus forming an interlocking connection between the base 400 and the lens 500. It also is contemplated that actuatable tab 506 may be inserted into recess 412, and may be actuated between the compressed position to facilitate entry of fixed tab 504 into recess 412, and the uncompressed extended position to insert fixed tab 504 further into recess 412 to form the interlocking connection between base 400 and lens 500.

Actuatable tab 506 may include two members 510 and 512, each with one end connected to the edge of the optic 502, and the other end free, thus forming two cantilever springs. A rim 514 may extend around the perimeter of the optic 502, terminating shy of the springs 510 and 512, thus allowing the springs 510 and 512 to fully compress against the edge of the optic 502. The rim 514 of the lens 500 may have an outside diameter that is greater than the inside diameter of the posterior rim 408 of the base 400 such that the lens 500 doesn't fall through the opening 404 of the base 400 and such that the lens 500 is circumferentially supported around its perimeter by the posterior rim 408 of the base 400. A gusset with a guide hole 516 may be disposed between the two members 510 and 512 to facilitate manipulation by a probe. Similarly, a guide hole 508 may be provided in the fixed tab 504 to provide access for a probe (e.g., Sinskey hook) or similar device to manipulate the fixed tab 504 into the recess 412 in the base 400. A notch 518 may be provided in the fixed tab 504 to provide asymmetry as a visual indicator that the anterior side is up (rather than down) when the notch is counter-clockwise of the hole 508.

As seen in FIG. 5C, the anterior and posterior sides of the optic 502 may have convex radii corresponding to the desired power (Diopter) of the optic. The fixed tab 504 and the spring tabs 510 and 512 may have a flared cross-section as shown. More specifically, and as better seen in the detailed view shown in FIG. 5D, the fixed tab 504 extends radially outward from the optic 502 from a thinner inner portion 504B to a flared thicker outer portion 504A. Hole 508 may extend through thinner inner portion 504B. The outermost profile of the thicker portion 504A has a squared profile with an anterior horizontal side, a posterior horizontal side, and a lateral or outer vertical side that are keyed to the recess 412 as described previously to minimized anterior-posterior and radial/lateral movement of the lens 500 relative to the base 400. The thicker portion 504A also provides for improved engagement with the plunger of an injector to mitigate jamming of the lens 500 in the injector. The thinner portion 504B also provides an anterior and a posterior offset from the surfaces defining the recess 412 of the base 400, thereby mitigating adhesion between the lens 500 and the base 400. The same flared configuration and associated advantages also applies to each of the spring tabs 510 and 512 as shown.

Commercially available IOLs typically have an equatorial diameter (excluding haptics) of about 6 mm, an anterior-posterior thickness of about 0.2 mm at 6 mm diameter and 0.7 mm at the center, providing an overall volume of about 12 mm3. Lens 500 is similarly dimensioned, but the base 400 adds substantially more volume. The base 400 may have an equatorial diameter (excluding haptics) of about 7.8 mm, an anterior-posterior thickness of about 1 mm, providing an overall volume of about 26 cubic millimeters [13.4 $mm^3$ base, 12.5 $mm^3$ optic] when the lens is disposed into the base. Thus, the size of the combined base 400 and lens 500 is volumetrically much larger than conventional IOLs available on the market. This relatively larger volume is intended to fill the capsular bag more like a natural lens, thus increasing the stability of the modular IOL 300 and reducing post-operative migration due to the bag collapsing around the base 400. By way of comparison, a typical natural lens has an equatorial diameter of about 10.4 mm, an anterior-posterior dimension of about 4.0 mm for a corresponding volume of about 180 mm3. Due to anatomic variability, a natural lens may have a volume ranging from 130 mm$^3$ to 250 mm$^3$. Thus, the modular IOL 300 (base 400 plus lens 500) consumes greater than 10% (about 20% to 10.4%) of the volume of the bag after the natural lens has been extricated, whereas a conventional IOL consumes less than or equal to 10% (about 10% to 5%) of the volume of the bag. In other words, the modular IOL 300 consumes about twice the volume of the bag compared to a conventional IOL.

Also by comparison to conventional IOLs, modular IOL 300, by virtue of the annular ring 402 of the base 400, provides a relatively large diameter and rigid platform that resists deflection (i.e., increased stiffness in the sagittal plane, thereby improving anterior-posterior stability). Coupled with the relatively long sweeping haptics 406 which offer a significant relative increase in surface contact with the capsular bag, the modular IOL 300 provides superior centering and stability within the capsular bag.

Figure 3B:
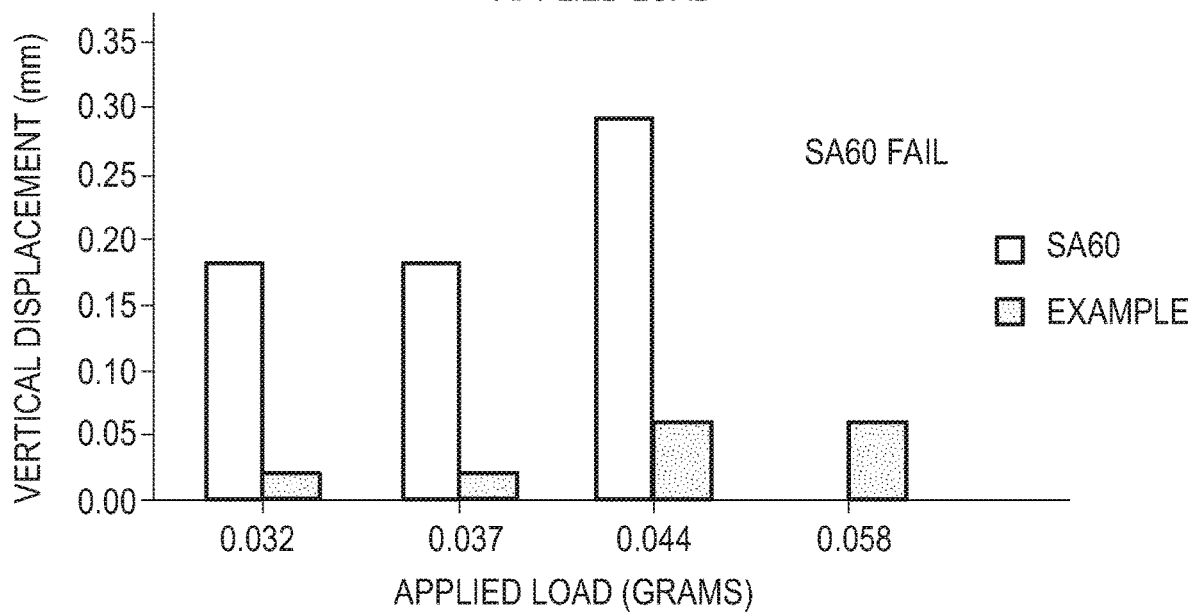
FIG. 3B is a chart of the results of a bench test comparing the performance of the modular IOL shown in FIG. 3A to a commercially available IOL.

The ability to resist deflection was demonstrated in a bench test comparing the performance of modular IOL 300 to a commercially available IOL (Alcon model SA60), the results of which are shown in FIG. 3B. In the test set-up, the test IOL was placed in a 10 mm inside diameter simulated capsular bag and the assembly was submerged in a warm bath. Various loads were applied to the middle of test IOL while in a horizontal orientation, and the resulting downward displacement was measured. As can be seen from the results shown in FIG. 3B, the commercially available IOL was displaced roughly 5 times the amount that the modular IOL 300 was displaced, and the commercially available IOL failed to support a load of 0.058 grams as the haptics were displaced out of the simulated capsular bag. This demonstrates the significant relative increase in stiffness of modular IOL 300 compared to a common commercially available IOL.

This test set-up may be compared to a mechanical model of a center load on beam with two simple supports described by $F=k_{eq}\Delta x$, where F=applied force, $k_{eq}$=equivalent stiffness and $\Delta x$=displacement. Equivalent stiffness takes into account the cross-sectional moment of inertia of the beam as well as the material properties of the beam (Young's elastic modulus). However, since IOLs are made of plastic (rather than an elastic material such as metal), the equivalent stiffness will vary over a range of applied forces. In the described bench test, the modular IOL 300 had an equivalent stiffness of approximately 0.5 to 2.0 g/mm over a range of applied loads of 0.032 to 0.100 g, whereas the commercially available IOL had an equivalent stiffness of approximately 0.15 to 0.20 g/mm over a range of applied loads of 0.032 to 0.044 g.

In general, when the base 400 and lens 500 are assembled to form modular IOL 300, the features may be configured such that the mid-plane of the optic 502 is parallel with the mid-plane of the base 400, and the central (anterior-posterior) axis of the optic 502 is coincident and collinear with the central (anterior-posterior) axis of the base 400. Assuming anatomic symmetry of the native lens capsule and centration of the base 400 in lens capsule, this configuration essentially aligns the central axis of the optic 502 with the central (anterior-posterior) axis of the capsular bag, thus providing centration of the optic 502. However, there may be instances where the visual (foveal) axis is not aligned with the anatomic (pupillary axis), wherein the difference is called angle of kappa. In such instances, it may be desirable to offset the central axis of the optic 500 relative to the base 400, thus providing de-centration. This may be accomplished, for example, by configuring the tabs 504 and 506, the recess 412 and/or the haptics 406 such that the central (anterior-posterior) axis of the optic 502 is laterally (nasally or temporally) offset relative to the central (anterior-posterior) axis of the base 400.

By way of example, not limitation, the lateral walls defining the recess 412 in the base 400 may be offset relative to the haptics 406 so that the central axis of the optic 502 is offset. Different offsets could be provided, for example, 0.5 mm through 2.0 mm at 0.5 mm increments. Angular orientation marks on the base 400 and lens 500 may be provided to indicate the direction of the offset (nasally or temporally). Similarly, the mid-plane of the assembled base 400 and optic 500 may be tilted relative to the equatorial plane of the native capsular bag. To compensate for this tilt, for example, the tabs 504 and 506, the recess 412 and/or the haptics 406 may be configured such that the mid-plane of the optic 502 is counter-tilted.

The base 400 and lens 500, including the alternative embodiments described herein, may be formed by cryogenically machining and polishing hydrophobic acrylic material. Optionally, the base 400 may be manufactured by forming two (anterior and posterior) components and adhesively connecting them together. For example, the two components may be cryogenically machined hydrophilic acrylic connected together by a U.V. curable adhesive. Alternatively, the two components may be formed of different materials adhesively connected together. For example, the anterior component may be formed of hydrophilic acrylic which does not adhere to ocular tissue, and the posterior component may be formed of hydrophobic acrylic which does adhere to ocular tissue.

As a further alternative, the base 400 may be manufactured by cryogenic machining the first component and over-molding the second component. The first component may include geometric features that become interlocked when over-molded, thus mitigating the need for adhesive to connect the components. For example, the base 400 may be manufactured by cryogenic machining of hydrophilic acrylic to form the posterior component, and over-molding the anterior component of a moldable material such as silicone.

While hydrophobic acrylic renders the base 400 and lens 500 visible using optical coherence tomography (OCT), it may be desirable to incorporate a material that enhances OCT visualization. Example "OCT-friendly" materials include but are not limited to polyvinyl chloride, glycol modified poly (ethylene terephthalate) (PET-G), poly (methyl methacrylate) (PMMA), and a polyphenylsulfone, such as that sold under the brand name RADEL™, as described in U.S. Patent Application Publication No. 2013/0296694 to Ehlers et al., which is incorporated herein by reference. Such OCT-friendly materials may be applied to or incorporated into a portion of the base 400 or lens 500.

By way of example, a concentric ring of OCT-friendly material may be applied to each of the lower and upper rims 408/410. The rings may have different diameters to aid in detecting tilt of the base. Also by way of example, OCT-friendly material may be applied to the tabs 504/506 of the lens 500. This may aid in determining if the base 400 and lens 500 are correctly assembled in the eye. Points of OCT-friendly material may be applied to portions of the base 400 that line up to corresponding OCT-friendly points on the optic 500 to indicate proper assembly in the eye.

As an alternative to solid material, the base 400 and lens 500 may be made of hollow material that can be subsequently inflated in the eye. In this arrangement, the base 400 and lens 500 may be made from molded silicone, for example, and inflated with a liquid such as saline, silicone gel or the like using a syringe and needle. The needle may pierce the wall of the base 400 and lens 500 after implantation in the eye to inflate the components. The material may self-seal after removal of the needle. As an alternative to a hollow material, the base 400 and lens 500 may be formed of a sponge-like material such as silicone hydrogel that swells upon hydration. Both approaches allow the size of the corneal incision to be smaller, as the base 400 and lens 500 are delivered in an uninflated or unswelled state and subsequently inflated or swelled once inside the eye.

In general, the modular IOL 300, comprising the assembled base 400 and lens 500, including the alternative embodiments described herein, allows for the lens 500 to be adjusted or exchanged while leaving the base 400 in place, either intra-operatively or post-operatively. Examples of instances where this may be desirable include, without limitation: exchanging the lens 500 to correct a suboptimal refractive result detected intra-operatively; exchanging the lens 500 to correct a suboptimal refractive result detected post-operatively (residual refractive error); rotationally adjusting the lens 500 relative to the base 400 to fine tune toric correction; laterally adjusting the lens 500 relative to the base 400 for alignment of the optic with the true optical axis (which may not be the center of the capsular bag); and exchanging the lens 500 to address the changing optical needs or desires of the patient over longer periods of time. Examples of the latter instance include, but are not limited to: an adult or pediatric IOL patient whose original optical correction needs to be changed as s/he matures; a patient who wants to upgrade from a monofocal IOL to a premium IOL (toric, multifocal, accommodating or other future lens technology); a patient who is not satisfied with their premium IOL and wants to downgrade to monofocal IOL; and a patient who develops a medical condition where an IOL or a particular type of IOL is contra-indicated.

Figure 6A:
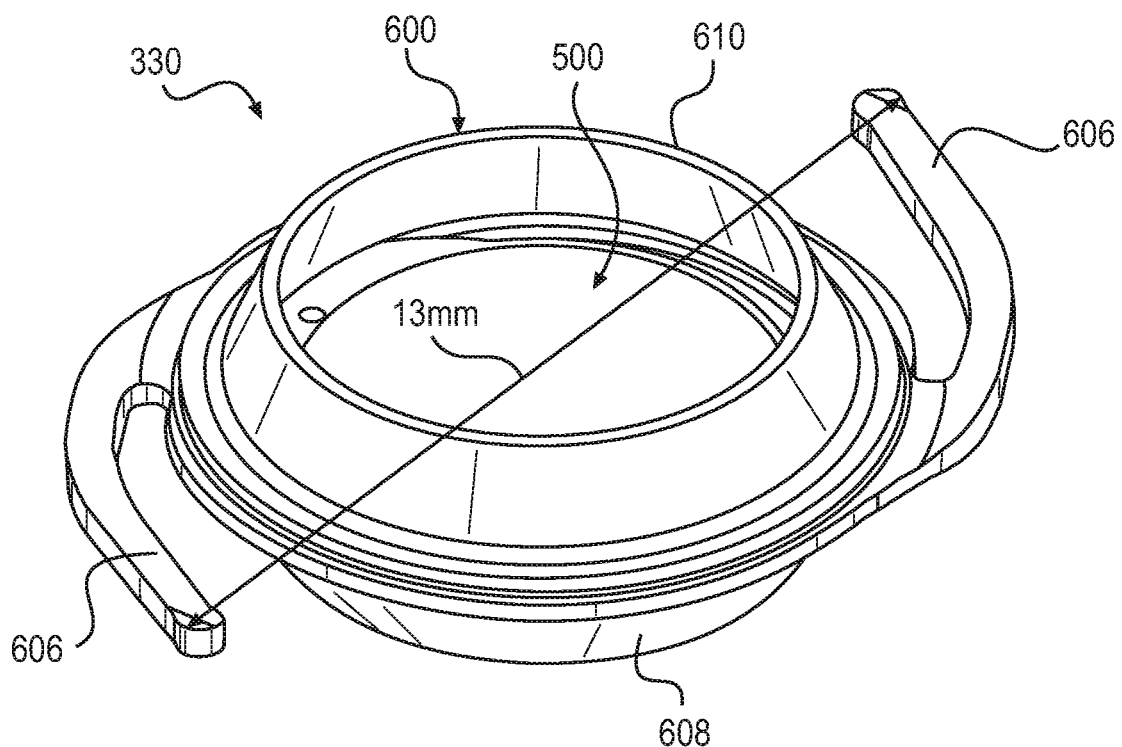
FIGS. 6A and 6B are perspective and cross-sectional views, respectively, of an alternative modular IOL according to the present disclosure.
Figure 6B:
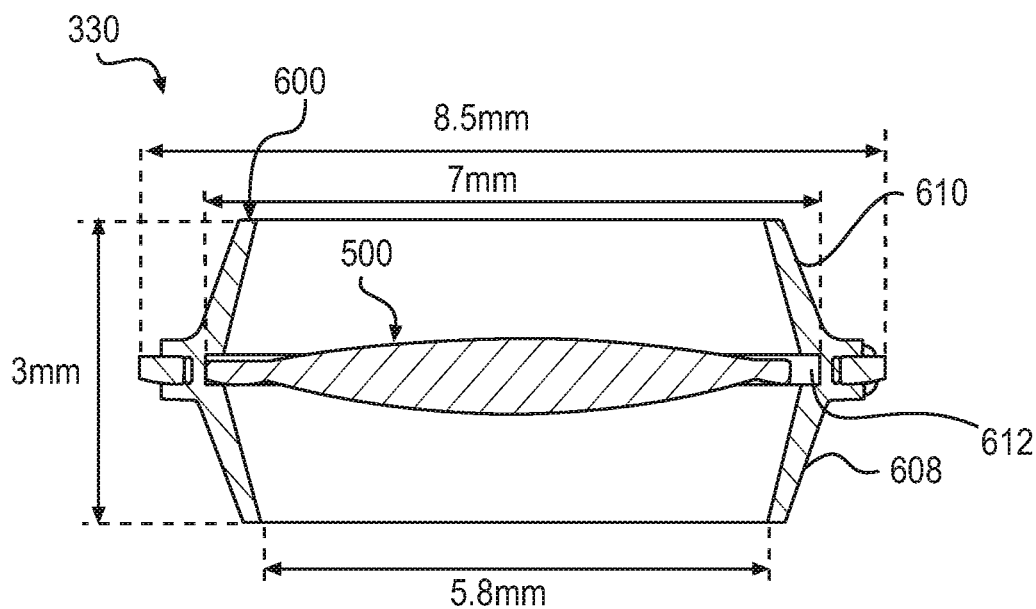

With reference to FIGS. 6A and 6B, an alternative modular IOL 330 is shown in perspective and cross-sectional views, respectively. Alternative modular IOL 330 may include an alternative base 600 and the lens 500 as described above. As will be appreciated by the following description, alternative base 600 may be similar to base 400 except for anterior rim 610 and posterior rim 608, the description of the similar aspects and advantages being incorporated herein by reference. Alternative base 600 includes an annular ring defining a center hole. A pair of haptics 606 extend radially outward from the annular ring. The annular ring includes a lower rim 608, an upper rim 610 and an inward-facing recess 612, into which the lens 500 may be inserted to form modular IOL 330.

With specific reference to FIG. 6B, the lower rim 608 and upper rim 610 may have a relatively exaggerated height and may be angled radially inward to form a funnel leading to the recess 612. With this arrangement, the actuatable tabs 506 of the lens may be compressed and the lens 500 may be placed through the circular opening defined by the anterior rim 610, with the funnel shape of the anterior rim 610 guiding the tabs 504 and 506 into the recess 612 of the base 600 to form a keyed geometry to limit movement of the lens 500 relative to the base 600 in anterior, posterior and radial directions. The funneled shape of the posterior rim 608 prevents the lens 500 from falling posteriorly during insertion of the lens 500 into the base 600.

The base 600 may have the dimensions as shown by way of example, not necessary limitation. As best seen in FIG. 6B, the rims 608 and 610 of the base 400 may have a combined anterior-posterior height that is 2.0 to 3.0 (or more) times the maximum thickness of the optic portion 502 of the lens 500. For example, the combined height of the rims 608 and 610 may be approximately 3 mm at a radial distance of approximately 2.9 mm from the center point. As described previously, the height of posterior rim 608 may be made greater than the height of anterior rim 610 such that the sagittal mid-plane of the base 600 is aligned (+/−0.5 mm) with the equatorial plane of the lens 30 when the modular IOL 330 is implanted in the capsular bag. The height ratio of the anterior rim 610 to the posterior rim 608 may be constant at a value less than 1.0 such as approximately 0.7 (±0.3), for example. As shown, the combined height of the anterior rim 610 and the posterior rim 608 are selected such that the anterior-most portion of the anterior rim 610 is in close proximity (within 0.5 mm) to or pushing against the anterior side 33 of the lens 30 and the posterior-most portion of the posterior rim 608 is in close proximity (within 0.5 mm) to or pushing against the posterior side 35 of the lens 30 when implanted in the capsular bag.

Figure 7A:
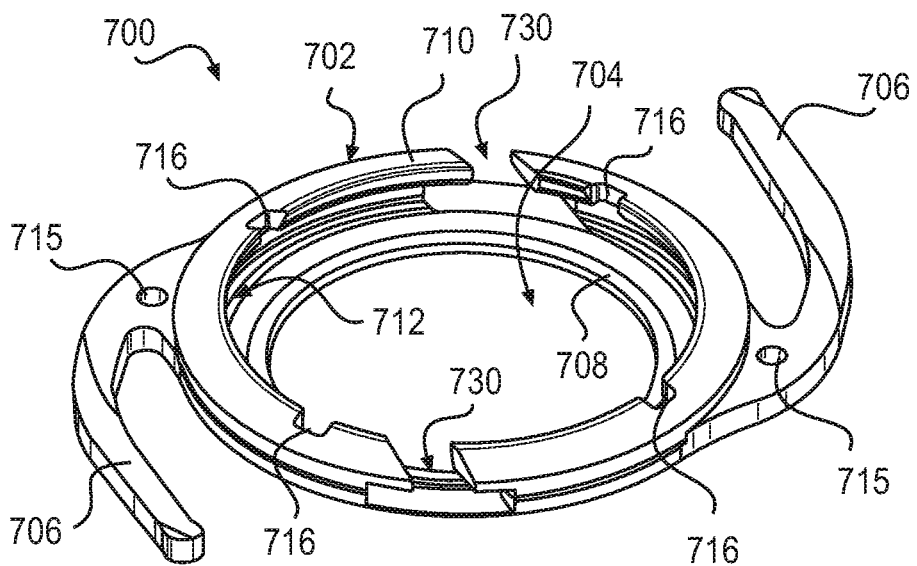
FIGS. 7A-7B are perspective views of an alternative base for use with a conventional IOL according to the present disclosure.
Figure 7B:
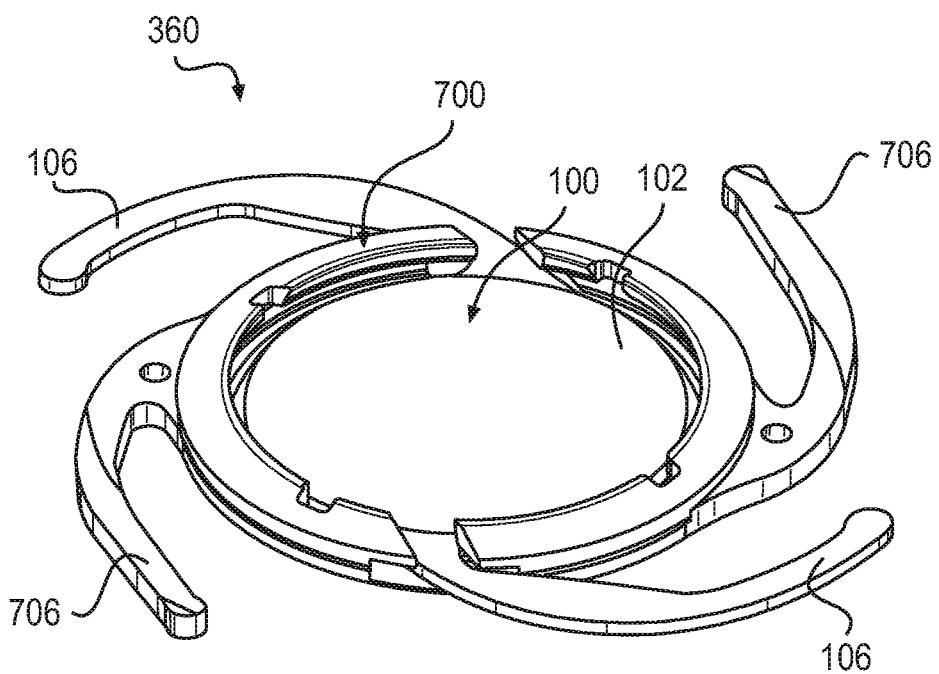

With reference to FIGS. 7A and 7B, an alternative base 700 for use with a conventional IOL 100 is shown in perspective views, where FIG. 7A shows the base 700 standing alone and FIG. 7B shows the combined base 700 and conventional IOL 100 assembled to form modular IOL 360. Alternative base 700 is similar to base 400 described previously, with the exception of inverted T-slots 730, the description of the similar aspects and advantages being incorporated herein by reference.

The base 700 includes an annular ring 702 defining a center hole 704. A pair of haptics 706 extend radially outward from the annular ring 702. The annular ring 702 includes a lower rim 708, an upper rim 710 and an inward-facing recess 712, into which the conventional IOL 100 may be inserted to form modular IOL 360. The upper rim 710 of annular ring 702 may include one or more notches 716 to provide access for a probe (e.g., Sinskey hook) intra-operatively, which allows the base 700 to be more easily manipulated. The haptics 706 may include holes 715 adjacent the annular ring 702 for the same purpose as notches 716.

The annular ring 702 may include a pair of inverted-T-shaped slots 730 to accommodate the diametrically opposed haptics 106 of the conventional IOL 100. When the haptics 106 of the conventional IOL 100 are placed in the slots 730, the posterior side of the optic portion 102 of the conventional IOL 100 may rest upon the anterior surface of the posterior rim 708. The posterior portion of the slots 730 may have a greater width than the anterior portion thereof to accommodate the angle of the haptics 106 and to lock the IOL 100 to the base 700 when rotated relative thereto. The addition of the base 700 adds to the anterior-posterior rigidity and height of a conventional IOL 100, thereby improving its stability.

Figure 8A:
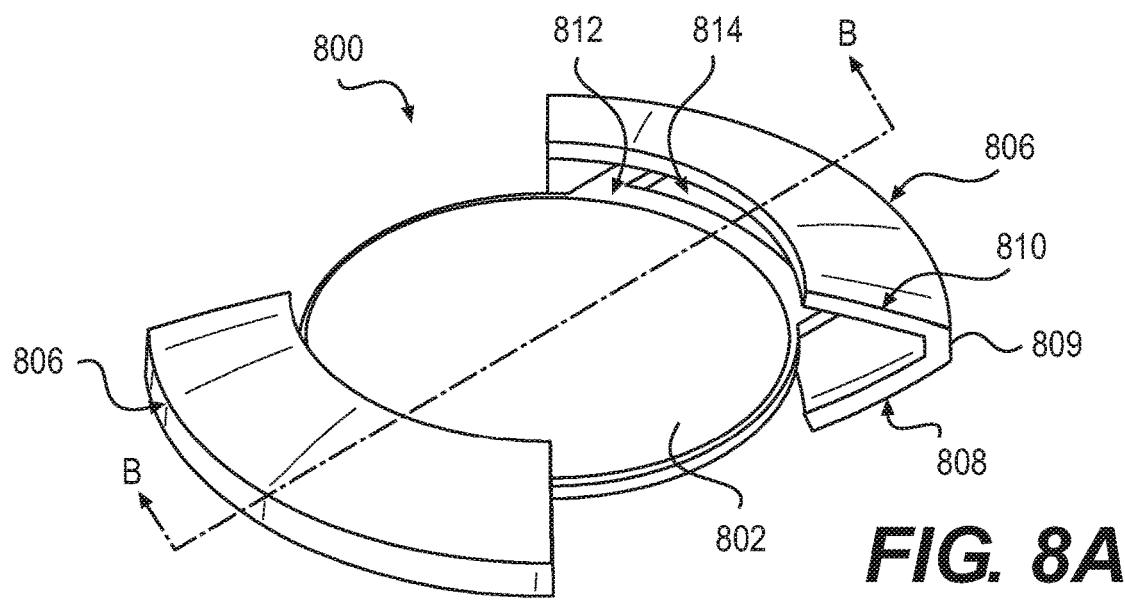
FIGS. 8A-8C are perspective, cross-sectional and top views, respectively, of a non-modular IOL according to the present disclosure.
Figure 8B:
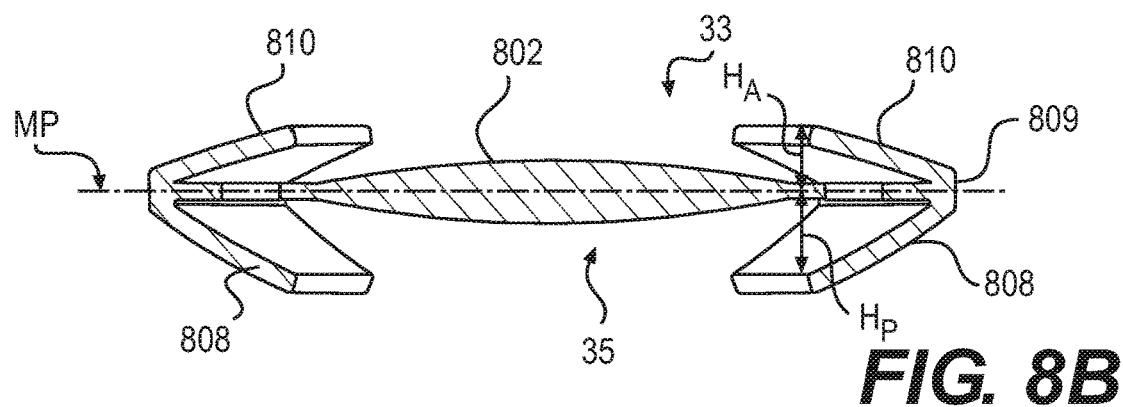
Figure 8C:
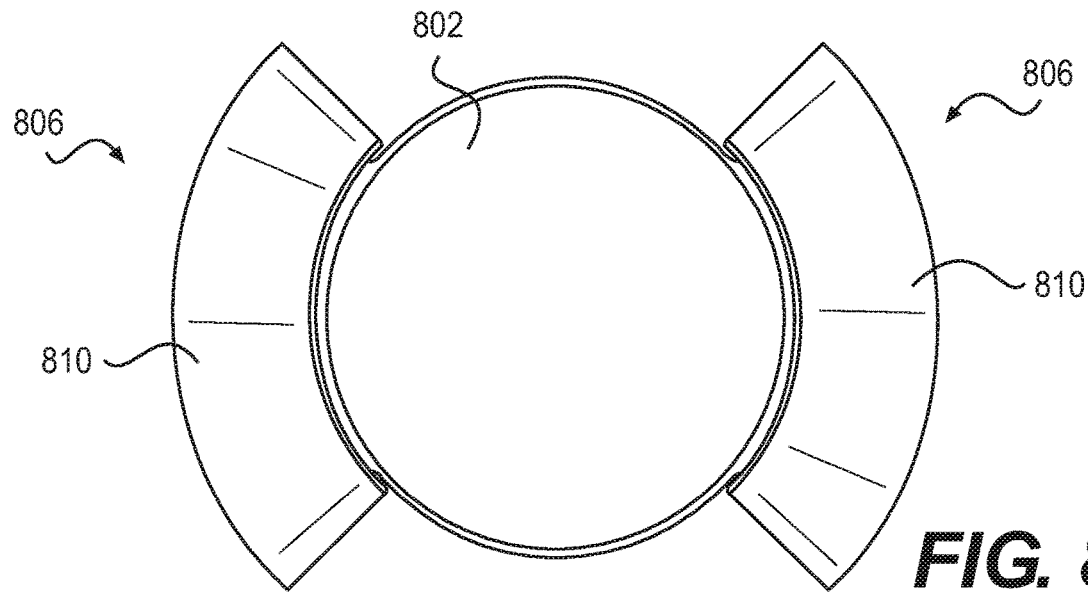

With reference to FIGS. 8A-8C, perspective, cross-sectional and top views, respectively, of a non-modular IOL 800 is shown schematically. Non-modular IOL 800 incorporates several of the stability advantages described previously, but in a non-modular configuration. IOL 800 includes an optic portion 802 that may be monofocal (fixed focal length), accommodating (variable focal length), toric, multifocal, or extended depth-of-focus pattern, for example. IOL 800 also includes two or more haptics 806 extending radially outward from the periphery of the optic portion 802. Each haptic includes a posterior flange 808 and an anterior flange 810 extending radially inward and flared in an outward posterior and an outward anterior direction, respectfully, from an outer rim 809. Each haptic 806 includes a connecting arm 812 that connects the outer rim 809 to the periphery of the optic 802. Each connecting arm 812 may include a window 814 for added flexibility. The posterior flange 808 and the anterior flange 810 are configured to compress relative to each other in an anterior-posterior direction, acting like cantilever leaf springs about outer rim 809.

With specific reference to FIG. 8B, which is a cross-sectional view taken along line B-B in FIG. 8A, it can be appreciated that the posterior flange 808 is sized and configured differently than anterior flange 810 in order to conform to the shape of the capsular bag. As described previously, the posterior thickness of the native lens is greater than the anterior thickness of the native lens. In order for the anterior flange 810 to conform to the anterior side 33 of the lens capsule and the posterior flange 808 to conform to the posterior side 35 of the lens capsule, the anterior flange 810 may have an anterior height $H_A$ and arc length that is less than the posterior height $H_P$ and arc length of the posterior flange 808. For example, $H_P$ may be made greater than $H_A$ such that the sagittal mid-plane MP of the base 800 is aligned (+/−0.5 mm) with the equatorial plane of the lens capsule when the IOL 800 is implanted in the capsular bag. The ratio $H_A/H_P$ may be constant at approximately 0.7 (±0.3), for example.

With specific reference to FIGS. 8B and 8C, the radial length (in the sagittal plane) of the posterior flange 808 and anterior flange 810 may be selected such that the inner-most edge does not interfere with the field of vision through the optic 802. In other words, the posterior flange 808 and the anterior flange 810 may extend radially inward from the outer rim 809 up to the outer diameter of the optic portion 802, where the inner edge of the posterior flange 808 and the anterior flange 810 forms an arc conforming to the outside diameter of the optic 802. The outer rim 809 may also form an arc, wherein the haptics 806 conform the circular shape of the equator of the natural lens capsule. By way of example, not necessarily limitation, the arc shape of the haptics 806 may extend 60°-90°, 90°-120°, or 120°-150° around the circumference of the optic 802. The larger the arc length of the haptics, the greater the contact area with the equator of the natural lens capsule, the greater the stability of the IOL 800 in the capsular bag, but this must be balanced against the deliverability of the IOL 800 through a small incision using an injector.

Figure 9A:
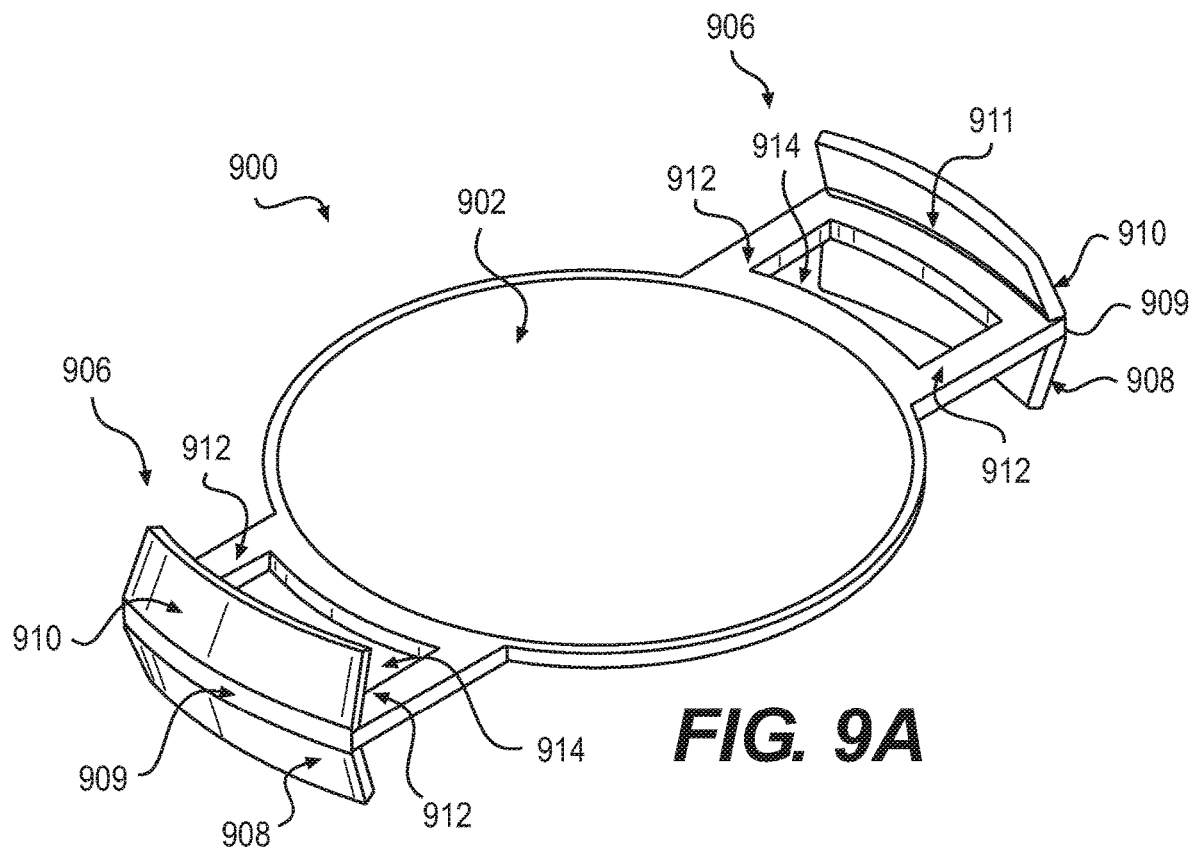
FIGS. 9A and 9B are perspective views of alternative non-modular IOLs according to the present disclosure.
Figure 9B:
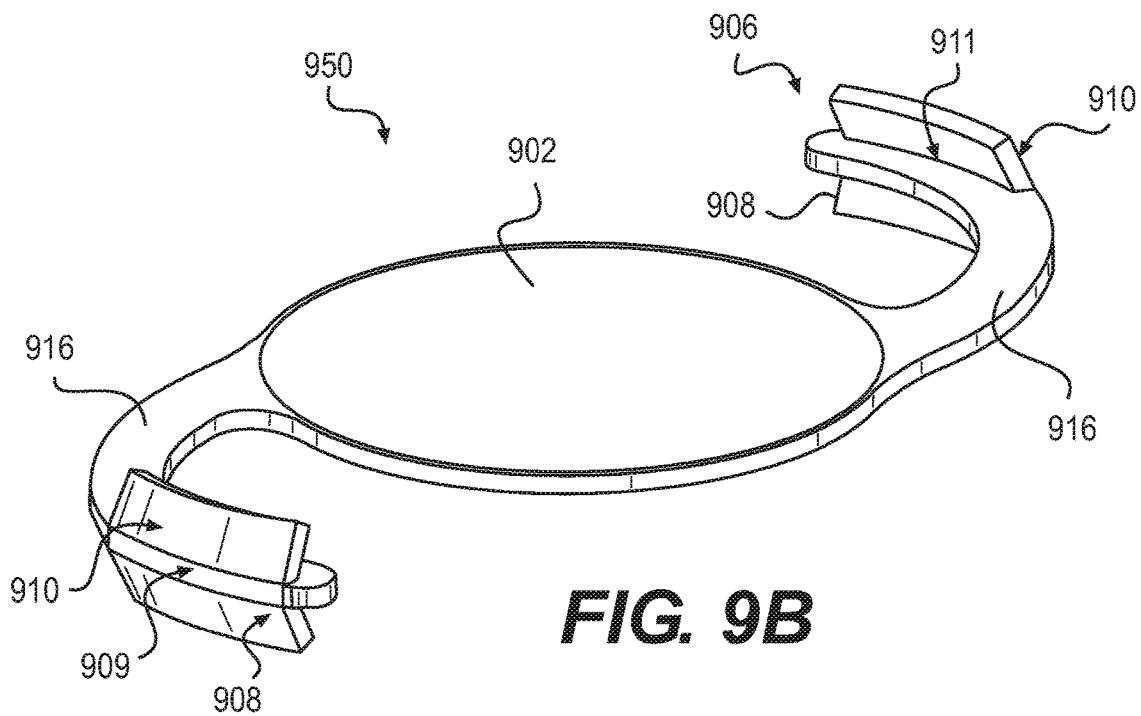

With reference to FIGS. 9A and 9B, alternative non-modular IOLs 900 and 950, respectively, are shown in perspective view. IOLs 900 and 950 are similar to IOL 800 described above in that the haptics include flared flanges for improved stability; the description of the similar aspects and advantages being incorporated herein by reference.

With specific reference to FIG. 9A, IOL 900 includes an optic portion 902 that may be monofocal (fixed focal length), accommodating (variable focal length), toric, multifocal, or extended depth-of-focus pattern, for example. IOL 900 also includes two or more haptics 906 extending radially outward from the periphery of the optic portion 902. Each haptic 906 includes a posterior flange 908 and an anterior flange 910 extending radially inward and flared in an outward posterior and an outward anterior direction, respectfully, from an outer rim 909. Each haptic 906 includes a pair of connecting arms 912 that connect the outer rim 909 to the periphery of the optic 902. Each pair of connecting arms 912 may include a window 914 for added flexibility. The posterior flange 908 and the anterior flange 910 are configured to compress relative to each other in an anterior-posterior direction, acting like cantilever leaf springs about outer rim 909. Compared to IOL 800, the flanges 908 and 910 of IOL 900 have a smaller radial length (in the sagittal plane) extending from the outer rim 909 toward the optic 902. In addition, a gap 911 is provided between the connecting arms 912 and the flanges 908 and 910 along the inside connection to the outer rim 909 to provide space for the flanges 908 and 910 to compress and fold down toward the optic 902. The gap 911 allows the connection between the outer rim 909 and the flanges 908 and 910 to function as a resilient hinge and allows the flanges 908 and 910 to better conform to the inside of the capsular walls that may vary in size and dimension.

With reference to FIG. 9B, IOL 950 is similar to IOL 900, the description of similar aspects and advantages being incorporated herein by reference. IOL 950 includes one or more haptics 906 including curvilinear arms 916 (rather than connecting arms 912) extending from the periphery of optic 902 to form the outer rim 909 from which the flanges 908 and 910 extend. As in the prior embodiment, a gap 911 is provided to enhance the flexibility of the flanges 908 and 910 relative to the curvilinear arms 916 along outer rim 909 such that the connection therebetween functions as a resilient hinge.

Figure 10A:
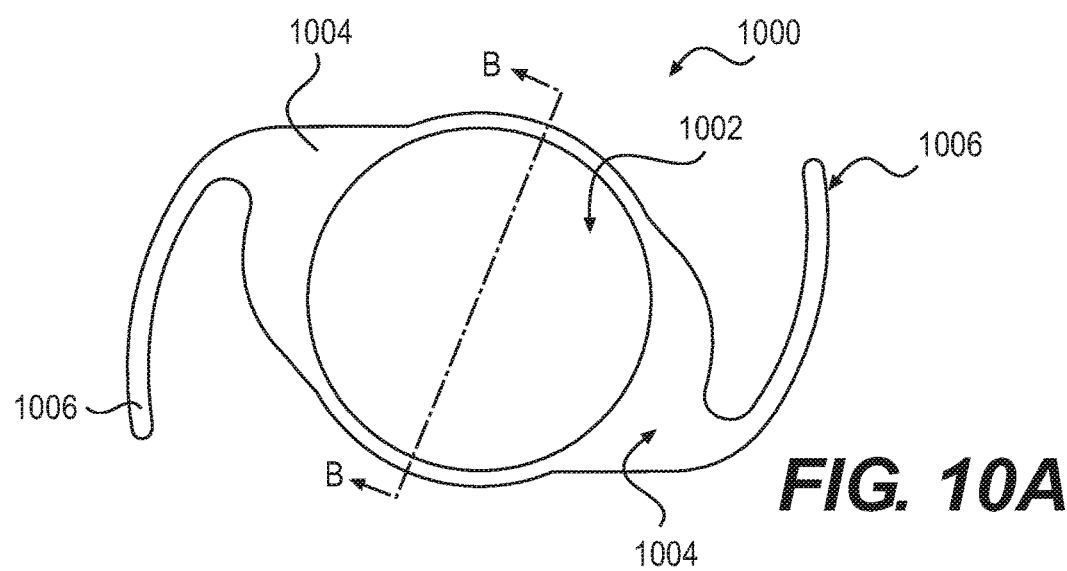
FIGS. 10A and 10B are top and cross-sectional views, respectively, of another alternative non-modular IOL according to the present disclosure.
Figure 10B:
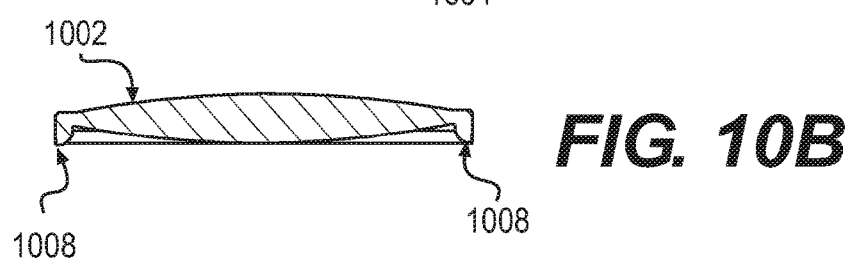

With reference to FIGS. 10A and 10B, an alternative non-modular IOL 1000 is shown schematically. FIG. 10A is a top view of the IOL 1000 and FIG. 10B is a cross-sectional view taken along line B-B in FIG. 10A. IOL 1000 includes an optic portion 1002 that may be monofocal (fixed focal length), accommodating (variable focal length), toric, multifocal, or extended depth-of-focus pattern, for example. IOL 1000 also includes a pair of haptics 1006 extending outwardly from the optic portion 1002. A pair of gusset plates 1004 connects the haptics 1006 to the optic portion 1002. Whereas a conventional IOL provides haptics extending from the optic portion, IOL 1000 utilizes the gusset plates 1004 to push the attachment location of the haptics 1006 radially outward, thereby relatively increasing the anterior-posterior stiffness of the IOL in the sagittal plane. IOL 1000 also includes a posteriorly extending ridge 1008 around the periphery of the optic 1002 and the periphery of the gusset plates 1004, excluding the haptics 1006 and the junction of the haptics 1006 to the gusset plates 1004. The ridge 1008 increases the cross-sectional moment of inertia of the IOL 1000 in the sagittal plane, thereby increasing its stiffness and stability, without affecting the flexibility of the haptics 1006. As seen in cross-section, the ridge 1008 may have an inside fillet and an outside square edge as shown, to inhibit cellular proliferation onto the optic portion 1002. By way of example, not necessarily limitation, the haptics may have an outside extent of 13 mm (haptic tip to haptic tip), the optic may have a diameter of 5 mm to 6 mm, and the gusset plates 1004 may have a mean sagittal width of 1 mm to 2 mm. Thus, with a 5.0 mm diameter optic 1002, the haptics 1006 may be attached to the gusset plates 1004 at a diameter of 7.0 mm to 9.0 mm.

Figure 11A:
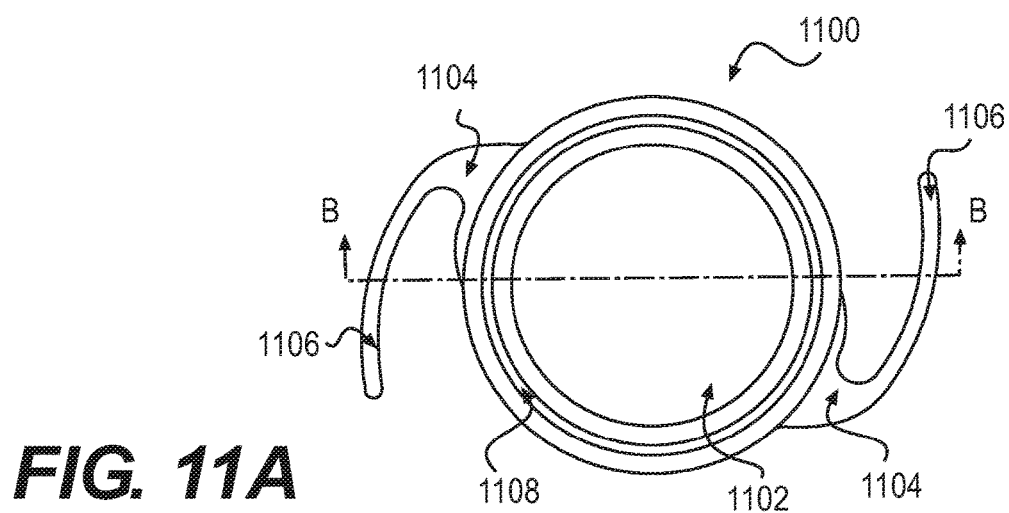
FIGS. 11A and 11B are top and cross-sectional views, respectively, of yet another alternative non-modular IOL according to the present disclosure.
Figure 11B:
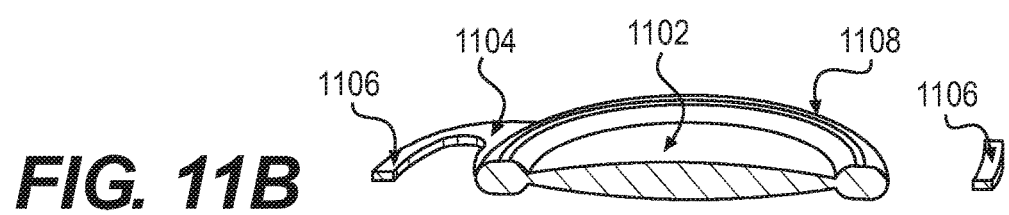

With reference to FIGS. 11A and 11B, another alternative non-modular IOL 1100 is shown schematically. FIG. 11A is a top view of the IOL 1100 and FIG. 11B is a cross-sectional perspective view taken along line B-B in FIG. 11A. As will be appreciated by the following description, IOL 1100 may be similar to IOL 1000 except with regard to ridge 1108, the description of the similar aspects and advantages being incorporated herein by reference. IOL 1100 includes an optic portion 1102 that may be monofocal (fixed focal length), accommodating (variable focal length), toric, multifocal, or extended depth-of-focus pattern, for example. IOL 1102 also includes a pair of haptics 1106 extending outwardly from the optic portion 1102. A pair of gusset plates 1104 connects the haptics 1006 to the optic portion 1102. Whereas a conventional IOL provides haptics extending from the optic portion, IOL 1100 utilizes the gusset plates 1104 to push the attachment location of the haptics 1106 radially outward, thereby relatively increasing the anterior-posterior stiffness of the IOL in the sagittal plane. IOL 1100 also includes a ridge 1108 that extends around the periphery of the optic 1102 and extends in both an anterior and a posterior direction. The ridge 1108 increases the cross-sectional moment of inertia of the IOL 1100 in the sagittal plane, thereby increasing its stiffness and stability, without affecting the flexibility of the gusset plates 1104 or the haptics 1106. As seen in cross-section, the ridge 1108 may be rounded in an oval shape.

Figure 12A:
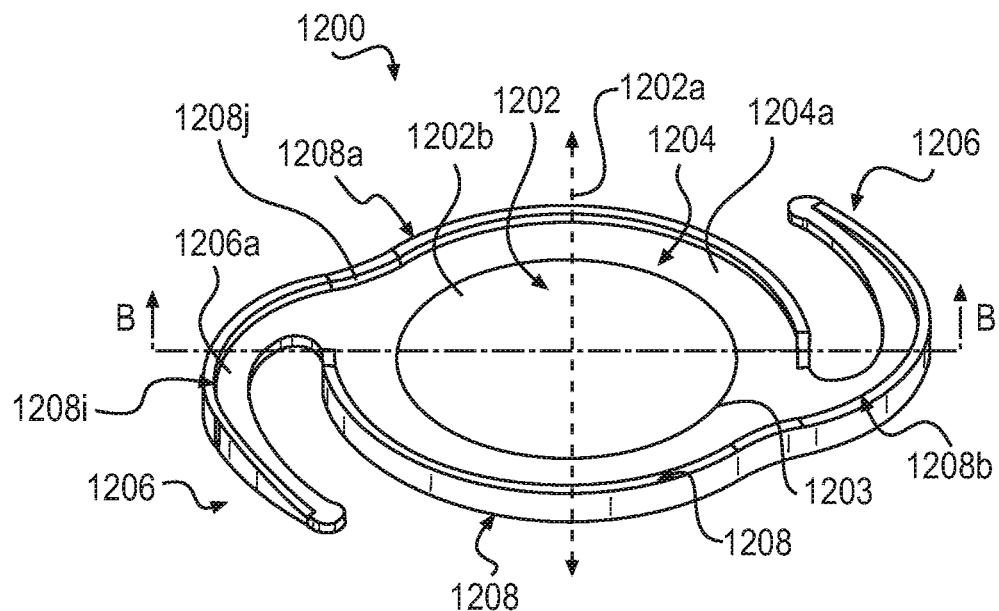
FIGS. 12A and 12B are top and cross-sectional views, respectively, of a further alternative non-modular IOL according to the present disclosure.
Figure 12B:
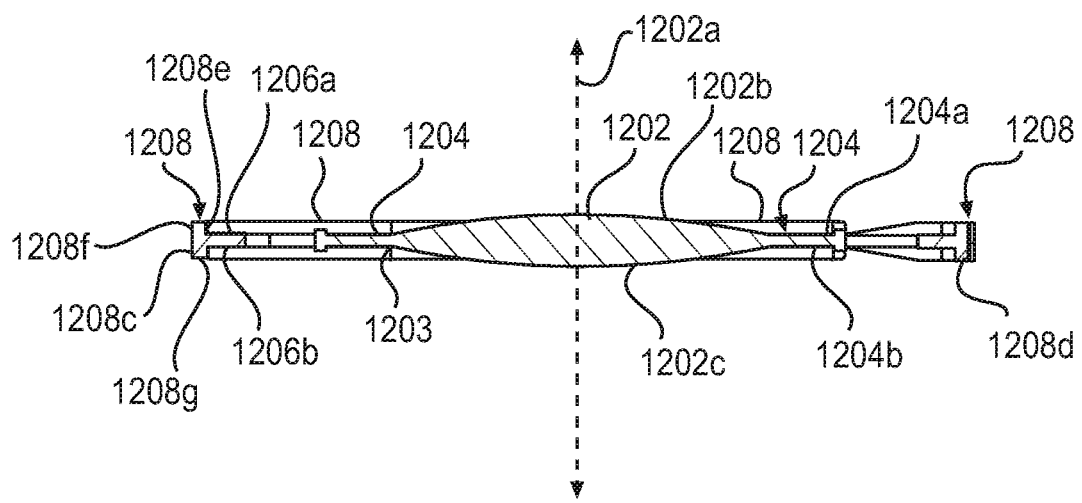

With reference to FIGS. 12A and 12B, yet another alternative non-modular IOL 1200 is shown schematically. FIG. 12A is a top view of the IOL 1200 and FIG. 12B is a cross-sectional view taken along line B-B in FIG. 12A. As will be appreciated by the following description, IOL 1200 may be similar to IOL 1000 except with regard to a gusset or support portion 1204 and one or more ridges 1208, the description of the similar aspects and advantages being incorporated herein by reference.

IOL 1200 includes an optic portion 1202 that may be monofocal (fixed focal length), accommodating (variable focal length), toric, multifocal, or extended depth-of-focus pattern, for example. IOL 1200 also includes a pair of haptics 1206 extending outwardly from the optic portion 1202. The or support portion 1204 extends around the periphery of the optic portion 1220 and connects the haptics 1206 to the optic portion 1202. Whereas a conventional IOL provides haptics extending from the optic portion, IOL 1200 utilizes the support portion 1204 to push the attachment location of the haptics 1206 radially outward, thereby relatively increasing the anterior-posterior stiffness of the IOL 1200 in the sagittal plane.

The support portion 1204 may surround the optic 1202. For example, the support portion 1204 may extend concentrically, a full 360°, around a radially-outer periphery of the optic 1202. In one example, the support portion 1204 may include an annular plate that forms a band around the optic 1202. The plate may have a substantially constant width between its inner and outer circumferences.

The support portion 1204 may include an anterior-facing surface 1204*a* and a posterior-facing surface 1204*b*. At least one of the anterior-facing and posterior-facing surfaces 1204*a* and 1204*b* of the support portion 1204 may extend substantially perpendicular to an optical axis 1202*a* of the optic 1202. Optic 1202 may have a curved anterior-facing surface 1202*b* and/or a curved posterior-facing surface 1202*c*. An annular concave region 1203 may be formed on the anterior and/or posterior sides of IOL 1200, where the support portion 1204 meets optic 1202, due to the angle formed between the anterior-facing surfaces 1204*a* and 1202*b* of the support portion 1204 and the optic 1202, respectively, and/or the angle formed between the posterior-facing surfaces 1204*b* and 1202*c* of the support portion 1204 and the optic 1202, respectively.

A thickness of the support portion 1204, measured between the anterior-facing and posterior-facing surfaces 1204*a* and 1204*b* of the support portion 1204, may be substantially equal to a thickness of the radially-outer periphery of the optic 1202 (measured between the peripheries of the anterior-facing and posterior-facing surfaces 1202*b* and 1202*c* of the optic 1202). Additionally or alternatively, the thickness of the support portion 1204 may be substantially equal to a thickness of the haptics 1206 (measured between anterior-facing and posterior-facing surfaces 1206*a* and 1206*b* of the haptics 1206).

IOL 1200 also may include one or more ledges or ridges 1208. The one or more ridges 1208 may extend around, along, and/or about one or more portions of the radially-outer peripheries of the support portion 1204 and haptics 1206. In one example, the one or more ridges 1208 may include one or more ridges that extend in an anterior direction from the anterior-facing surface 1204*a* of the support portion 1204. For example, the one or more anteriorly extending ridges my include a ridge 1208*a* and/or a ridge 1208*b*. Additionally or alternatively, the one or more ridges 1208 may include one or more ridges that extend in a posterior direction from the posterior-facing surface 1204*b* of the support portion 1204. For example, the one or more posteriorly extending ridges may include a ridge 1208*c* and/or a ridge 1208*d*. The one or more ridges 1208 may increase the cross-sectional moment of inertia of the entire IOL 1200 in the sagittal plane, including the optic 1202, support portion 1204 and haptics 1206, thereby increasing its stiffness and stability. While FIGS. 12A and 12B show a pair of anteriorly extending ridges 1208*a* and 1208*b* and a pair of posteriorly extending ridges 1208*c* and 1208*d*, it is contemplated that fewer ridges may be employed. For example, IOL 1200 may include only the anteriorly extending ridges 1208*a* and 1208*b*, or only the posteriorly extending ridges 1208*c* and 1208*d*.

As seen in cross-section in FIG. 12B, the one or more ridges 1208 may have a squared profile to mitigate cellular proliferation onto the optic 1202. For example, one or more of ridges 1208*a*, 1208*b*, 1208*c*, and 1208*d* may include opposing surfaces 1208*e* and 1208*f* that extend substantially perpendicular to the anterior-facing and/or posterior-facing surfaces 1204*a* and 1204*b* of the support portion 1204. Additionally or alternatively, opposing surfaces 1208*e* and 1208*f* may extend substantially parallel to one another. Additionally or alternatively, one or more of ridges 1208*a*, 1208*b*, 1208*c*, and 1208*d* may include an end surface 1208*g* that extends substantially parallel to the anterior-facing and/or posterior facing surfaces 1204*a* and 1204*b* of the support portion 1204. The surfaces 1208*f* may be flush with radially-outer peripheral surfaces of the support portion 1204 and/or the haptics 1206.

The ridge 1208*a* may extend on, along, or around the outside curvature of one of haptics 1206, and may be tapered (e.g., may taper down in height) at the tip of that haptic 1206 or proximate the tip of that haptic 1206. The tapered portion may define a first end of the ridge 1208*a*. The ridge 1208*a* may have a second end opposite its first end. The second end may be tapered (e.g., may taper down in height). The tapering at the second end of the ridge 1208*a* may have a greater slope than the tapering at the first end. Ridges 1208*b*, 1208*c*, and 1208*d* may be similarly shaped.

In between their tapered ends, ridges 1208*a*, 1208*b*, 1208*c*, and 1208*d* may have heights (measured in the anterior-posterior direction relative to surfaces of the support portion 1204) such that the anterior-facing surface 1202*b* of the optic 1202 may extend anterior to ridge 1208*a* and/or ridge 1208b, and/or the posterior-facing surface 1202c of the optic 1202 may extend posterior to ridge 1208c and/or ridge 1208d. It also is contemplated that one or more of ridges 1208a, 1208b, 1208c, 1208d may have a constant height in between its tapered ends.

As best seen in FIG. 12A, the ridges 1208a and 1208b may be discrete ridges, separated by a gap. Additionally or alternatively, the ridges 1208c and 1208d may be discrete ridges, separated by a gap. For example, an inside curvature of the haptics 1206 may exclude ridges to allow for radial compression of the haptics 1206 toward the optic portion 1202.

Ridge 1208a may include a first curved portion 1208h and a second curved portion 1208i. First and second curved portions 1208h and 1208i may be substantially concave, viewed from the perspective of optic 1202. Where first and second curved portions 1208h and 1208i meet they may form a convex portion 1208j of ridge 1208a. Ridges 1208b, 1208c, and/or 1208d may be similarly shaped.

The one or more ridges 1208 may be arranged in pairs. For example, ridges 1208a, 1208b may form a first, anterior pair or ridges, and/or ridges 1208c, 1208d may form a second, posterior pair of ridges. With respect to the pair of ridges 1208a and 1208b, an end portion of one of the ridges may extend past the opposing end portions of the other ridge and toward an intermediate portion of the other ridge. A similar arrangement may exist for pair of ridges 1208c and 1208d.

Figure 13A:
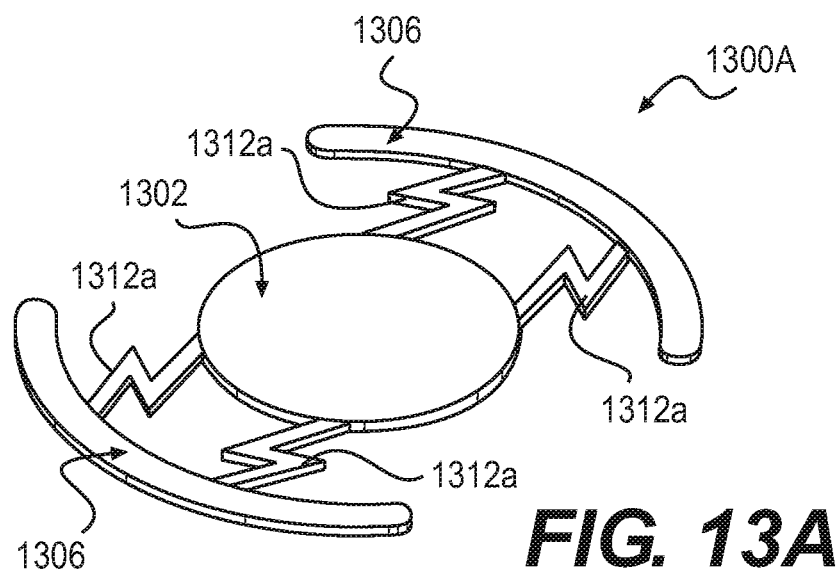
FIGS. 13A-13C are perspective views of various alternative non-modular IOLs according to the present disclosure.
Figure 13B:
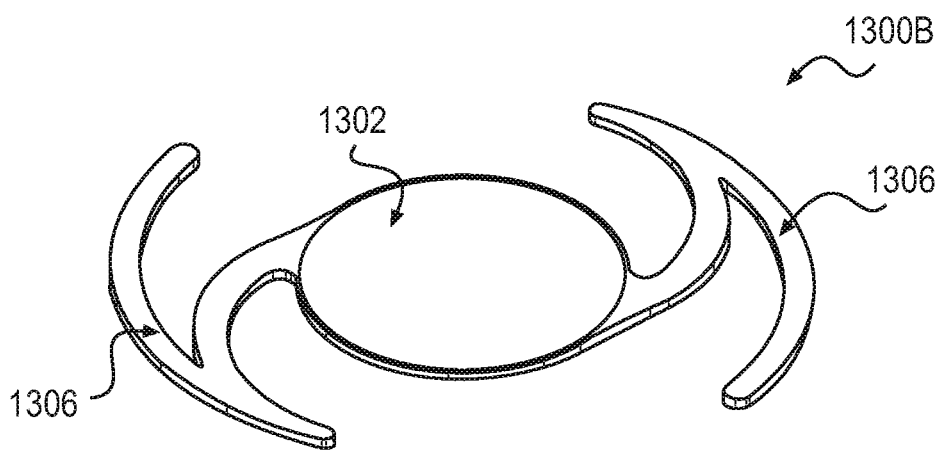
Figure 13C:
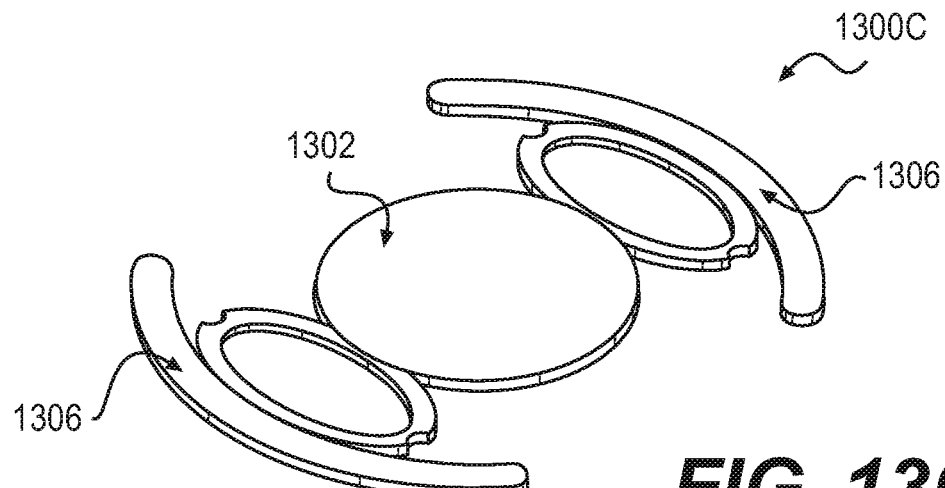

With reference to FIGS. 13A-13C, a variety of alternative non-modular IOLs 1300A, 1300B and 1300C are shown in perspective view. Each IOL 1300 includes an optic portion 1302 that may be monofocal (fixed focal length), accommodating (variable focal length), toric, multifocal, or extended depth-of-focus pattern, for example. Each IOL 1300 also includes two or more haptics 1306 connected to the optic portion 1302 via connecting arms 1312. By comparison to a conventional IOL where the haptics are curvilinear to provide radial spring force in addition to contact with inside equator of the lens capsule, connecting arms 1312 provide radial spring force independent of the haptics 1306, and haptics 1306 may be circular to maintain the same amount of contact area with the inside equator of the lens capsule independent of radial compression of the connecting arms 1312. This configuration provides more consistent stability of the IOL 1300 in the capsular bag, regardless of the size of the capsular bag. The haptics 1306 may extend 60°-90°, 90°-120°, or 120°-150° around the circumference of the optic 1302, and may have a constant radius of about 4.0 to 5.0 mm, for example. The connecting arms 1312 may be in the form of a multi-bar cantilever (zig-zag) spring 1312A, a single bar cantilever (curvilinear) spring 1312B, or a multi-leaf spring 1312C, for example.

The foregoing discussion of the disclosure has been presented for purposes of illustration and description. The foregoing is not intended to limit the disclosure to the form or forms disclosed herein. Although the disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

We claim:

1. A device configured for insertion into an eye, the device comprising:
    a base comprising:
        an anterior housing portion comprising:
            an anterior wall,
            an anterior opening at an anterior end of the anterior wall,
            an anterior chamber posterior to the anterior opening, wherein a width of the anterior chamber is greater than a width of the anterior opening,
        a posterior housing portion, and
        an intermediate housing portion extending between the anterior and the posterior housing portions, wherein the intermediate housing portion is wider than the anterior and the posterior housing portions and protrudes from the anterior and the posterior housing portions, and wherein the intermediate housing portion has a recess therein posterior to the anterior chamber, wherein the recess is a void of an inner surface of the intermediate housing portion,
    wherein the recess is spaced apart from the anterior opening by the anterior chamber and extends continuously around a circumference of the base, the void comprising an anterior ledge, a posterior ledge, and a sidewall extending in an anterior-posterior direction.

2. The device of claim 1, wherein the posterior housing portion comprises:
    a posterior wall;
    a posterior opening at a posterior end of the posterior wall; and
    a posterior chamber anterior to the posterior opening, wherein a width of the posterior chamber is greater than a width of the posterior opening, and wherein the recess is spaced apart from the posterior opening by the posterior chamber.

3. The device of claim 1, wherein each of the anterior housing, the posterior housing, and the intermediate housing portions is annular.

4. The device of claim 1, wherein the recess is annular.

5. The device of claim 1, wherein the recess is wider than the anterior chamber.

6. The device of claim 1, further including a lens configured for receipt in the recess.

7. The device of claim 6, wherein an anterior surface of the lens is spaced apart from the anterior opening by the anterior chamber when the lens is received in the recess.

8. A device configured for insertion into an eye, the device comprising:
    a base comprising:
        a first housing portion comprising:
            a first wall,
            a first opening at a first end of the first wall,
            a first chamber adjacent to the first opening, wherein a width of the first chamber is greater than a width of the first opening,
        a second housing portion, and
        an intermediate housing portion extending between the first and the second housing portions, wherein the intermediate housing portion is wider than the first and the second housing portions and protrudes from the first and the second housing portions, and wherein the intermediate housing portion has a recess therein adjacent to the first chamber, wherein the recess is a void of an inner surface of the intermediate housing portion,
wherein the recess is spaced apart from the first opening by the first chamber and extends continuously around a circumference of the base, the void comprising an anterior ledge, a posterior ledge, and a sidewall extending in an anterior-posterior direction.

9. The device of claim 8, wherein a radial thickness of the first wall is less than an axial height of the base.

10. The device of claim 8, wherein a radial thickness of the first wall is less than an axial height of the first wall.

11. The device of claim 8, wherein a radial wall thickness of the intermediate housing portion is less than an axial height of the base.

12. The device of claim 8, wherein the second housing portion comprises:
a second wall;
a second opening at a second end of the second wall; and
a second chamber adjacent to the second opening, wherein a width of the second chamber is greater than a width of the second opening, and wherein the recess is spaced apart from the second opening by the second chamber.

13. The device of claim 8, wherein a width of the first wall increases as the first wall approaches the intermediate housing portion.

14. The device of claim 8, further including a lens configured for receipt in the recess.

15. A device configured for insertion into an eye, the device comprising:
a base comprising:
an anterior housing portion comprising an anterior opening;
a posterior housing portion comprising a posterior opening;
an intermediate housing portion between the anterior and the posterior housing portions, the intermediate housing portion comprising a recess, wherein the recess is a void of an inner surface of the intermediate housing portion, the void comprising an anterior ledge, a posterior ledge, and a sidewall extending in an anterior-posterior direction, and wherein the recess extends continuously around a circumference of the base; and
a passage extending through the anterior housing, the posterior housing, and the intermediate housing portions, wherein the passage extends from the anterior opening to the posterior opening, wherein a radial width of the passage increases as the passage extends from the anterior opening through the anterior housing portion and to the intermediate housing portion, wherein the radial width further increases as the passage extends into the intermediate housing portion, and wherein the radial width decreases as the passage extends from the intermediate housing portion toward the posterior opening through the posterior housing portion.

16. The device of claim 15, further including a lens configured for receipt in the intermediate housing portion in the portion of the passage having the further increased radial width.

17. The device of claim 16, wherein the lens comprises:
a central optic; and
at least one extension protruding radially outwardly from the central optic, wherein the extension is configured to engage one or more surfaces of the intermediate housing portion that define the portion of the passage having the further increased radial width.

18. The device of claim 17, wherein the at least one extension includes a plurality of extensions.

19. The device of claim 18, wherein the plurality of extensions includes a pair of extensions protruding from diametrically opposite locations of the central optic.

20. The device of claim 16, wherein, when the lens is received in the intermediate housing portion, the device comprises:
an anterior chamber on an anterior side of the lens, radially surrounded by an anterior wall of the anterior housing portion, wherein the anterior chamber is wider than the anterior opening, and
a posterior chamber on a posterior side of the lens, radially surrounded by a posterior wall of the posterior housing portion, wherein the posterior chamber is wider than the posterior opening.

\* \* \* \* \*